(12) United States Patent
Schramm et al.

(10) Patent No.: US 7,622,073 B2
(45) Date of Patent: Nov. 24, 2009

(54) APPARATUS FOR AND METHOD OF DISPENSING ACTIVE MATERIALS

(75) Inventors: Heather R Schramm, Whitewater, WI (US); Jeffrey J Wolf, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 405 days.

(21) Appl. No.: 11/427,714

(22) Filed: Jun. 29, 2006

(65) Prior Publication Data
US 2007/0012718 A1    Jan. 18, 2007

Related U.S. Application Data

(63) Continuation-in-part of application No. 11/403,166, filed on Apr. 12, 2006.

(60) Provisional application No. 60/670,519, filed on Apr. 12, 2005.

(51) Int. Cl.
 A61L 9/04 (2006.01)
 A61L 9/12 (2006.01)
(52) U.S. Cl. .......................... 422/5; 422/123
(58) Field of Classification Search ............ None
See application file for complete search history.

(56) References Cited

U.S. PATENT DOCUMENTS

| | | | |
|---|---|---|---|
| 1,204,934 A | 11/1916 | Burford et al. | |
| 1,763,374 A | 6/1930 | Schrader | |
| 1,829,714 A | 10/1931 | McElroy et al. | |
| 1,947,752 A | 2/1934 | Benesh | |
| 2,084,682 A | 6/1937 | Guenot | |
| 2,094,161 A | 9/1937 | Paddock | |
| 2,103,609 A | 12/1937 | Bradburn | |
| 2,221,876 A | 11/1940 | Mackin | |
| 2,301,691 A | 11/1942 | Ellinger et al. | |
| 2,555,047 A | 5/1951 | Logue | |
| 2,600,877 A | 6/1952 | Jeffree | |
| 2,608,436 A | 8/1952 | Baughman | |
| 2,686,944 A | 8/1954 | Gubelin | |
| 2,741,004 A | 4/1956 | Williams | |
| 2,905,049 A | 9/1959 | Laube | |
| D191,396 S | 9/1961 | Weber, III | |

(Continued)

FOREIGN PATENT DOCUMENTS

AU    2005101048    2/2006

(Continued)

OTHER PUBLICATIONS

Yankee Candle web page http://www.yankeecandle.com/cgi-bin/ycbvp/product_detail.jsp?oid=3001476 1 page, printed May 15, 2007.

(Continued)

*Primary Examiner*—Elizabeth L McKane

(57) ABSTRACT

An apparatus for dispensing active materials comprises a housing and control circuitry disposed within the housing. The control circuitry implements programming for a mode of operation in which during a first period of time a first active material is emitted, during a second period of time the first active material and a second active material are emitted, and during a third period of time the second active material is emitted, wherein during the second period of time, the first and second fragrances are alternated.

17 Claims, 20 Drawing Sheets

U.S. PATENT DOCUMENTS

| | | |
|---|---|---|
| 3,118,610 A | 1/1964 | Techler |
| 3,172,604 A | 3/1965 | Brock |
| 3,301,486 A | 1/1967 | Brock |
| 3,370,571 A | 2/1968 | Kanpp |
| 3,370,951 A | 2/1968 | Knapp |
| 3,383,178 A | 5/1968 | Dietz |
| 3,410,488 A | 11/1968 | Sugimura |
| 3,447,505 A | 6/1969 | Wagner |
| 3,612,356 A | 10/1971 | McVey |
| 3,628,829 A | 12/1971 | Heilig |
| 3,655,135 A | 4/1972 | Altman et al. |
| 3,711,023 A | 1/1973 | Smith |
| 3,763,888 A | 10/1973 | Duecker |
| 3,812,996 A | 5/1974 | Bunnell |
| 3,844,057 A | 10/1974 | Johnson |
| 3,864,080 A | 2/1975 | Valbona et al. |
| 3,917,396 A | 11/1975 | Donohue etal. |
| 3,972,473 A | 8/1976 | Harrison |
| 4,006,841 A | 2/1977 | Alticosalian |
| 4,084,732 A | 4/1978 | Dearling |
| 4,229,415 A | 10/1980 | Bryson |
| 4,235,373 A | 11/1980 | Clark |
| 4,346,059 A | 8/1982 | Sector |
| 4,391,390 A | 7/1983 | Howard |
| 4,433,796 A | 2/1984 | Brooks, Jr. |
| 4,456,176 A | 6/1984 | Agius |
| 4,545,396 A | 10/1985 | Miller et al. |
| 4,556,539 A | 12/1985 | Spector |
| 4,580,721 A | 4/1986 | Coffee et al. |
| 4,603,030 A | 7/1986 | McCarthy |
| 4,614,300 A | 9/1986 | Falcoff |
| 4,629,164 A | 12/1986 | Sommerville |
| 4,629,604 A | 12/1986 | Spector |
| 4,680,060 A | 7/1987 | Gupta et al. |
| 4,695,434 A | 9/1987 | Spector |
| 4,755,404 A | 7/1988 | Collette |
| 4,790,479 A | 12/1988 | Matsumoto et al. |
| 4,804,821 A | 2/1989 | Glucksman |
| 4,846,403 A | 7/1989 | Mivelaz |
| 4,852,802 A | 8/1989 | Iggulden et al. |
| 4,870,991 A | 10/1989 | McMillan et al. |
| 4,878,615 A | 11/1989 | Losi |
| 4,881,568 A | 11/1989 | Ho |
| 4,889,285 A | 12/1989 | Locko |
| 4,893,615 A | 1/1990 | Khabirova |
| 4,901,890 A | 2/1990 | Mivelaz |
| 4,905,112 A | 2/1990 | Rhodes |
| 4,913,034 A | 4/1990 | Ripple et al. |
| 4,915,301 A | 4/1990 | Munteanu |
| 4,917,301 A | 4/1990 | Munteanu |
| 5,011,632 A | 4/1991 | Yano et al. |
| 5,021,701 A | 6/1991 | Takahashi et al. |
| 5,022,585 A | 6/1991 | Burgess |
| 5,023,020 A | 6/1991 | Machida et al. |
| 5,038,972 A | 8/1991 | Muderlak et al. |
| 5,050,798 A | 9/1991 | Sullivan |
| 5,071,621 A | 12/1991 | Tokuhiro et al. |
| 5,074,438 A | 12/1991 | Ingram |
| 5,086,978 A | 2/1992 | Fertig |
| 5,097,375 A | 3/1992 | Khan |
| 5,105,133 A | 4/1992 | Yang |
| 5,111,477 A | 5/1992 | Muderlak |
| 5,115,975 A | 5/1992 | Shilling |
| 5,133,498 A | 7/1992 | Sealy et al. |
| 5,152,397 A | 10/1992 | Mayled |
| 5,163,616 A | 11/1992 | Bernarducci et al. |
| 5,167,877 A | 12/1992 | Pai |
| 5,175,791 A | 12/1992 | Muderlak et al. |
| 5,178,327 A | 1/1993 | Palamand et al. |
| 5,186,869 A | 2/1993 | Stumpf et al. |
| 5,192,342 A | 3/1993 | Baron et al. |
| 5,193,744 A | 3/1993 | Goldstein |
| 5,201,025 A | 4/1993 | Landesberg |
| 5,212,672 A | 5/1993 | Loisch et al. |
| 5,227,068 A | 7/1993 | Runyon |
| 5,230,837 A | 7/1993 | Babasade |
| 5,234,162 A | 8/1993 | Sullivan |
| 5,314,619 A | 5/1994 | Runyon |
| 5,314,669 A | 5/1994 | Hamilton |
| 5,321,669 A | 6/1994 | Thayer et al. |
| 5,342,584 A | 8/1994 | Fritz et al. |
| 5,343,747 A | 9/1994 | Rosen |
| 5,364,027 A | 11/1994 | Kuhn |
| 5,377,363 A | 1/1995 | Shieh |
| RE34,847 E | 2/1995 | Muderlak et al. |
| 5,398,070 A | 3/1995 | Lee |
| 5,402,517 A | 3/1995 | Gillett et al. |
| D359,346 S | 6/1995 | Martin |
| 5,437,410 A | 8/1995 | Babasade |
| 5,449,117 A | 9/1995 | Muderlak et al. |
| 5,518,790 A | 5/1996 | Huber et al. |
| 5,524,609 A | 6/1996 | Krull |
| 5,534,229 A | 7/1996 | Nomura et al. |
| 5,565,148 A | 10/1996 | Pendergrass, Jr. |
| 5,591,409 A | 1/1997 | Watkins |
| 5,647,052 A | 7/1997 | Patel et al. |
| 5,658,387 A | 8/1997 | Reardon et al. |
| 5,660,330 A | 8/1997 | Scott |
| 5,666,987 A | 9/1997 | Combs |
| 5,695,692 A | 12/1997 | Kennedy |
| 5,724,256 A | 3/1998 | Lee et al. |
| 5,725,472 A | 3/1998 | Weathers |
| 5,727,186 A | 3/1998 | Shervington et al. |
| 5,734,590 A | 3/1998 | Tebbe |
| 5,762,268 A | 6/1998 | Shervington et al. |
| 5,772,074 A | 6/1998 | Dial et al. |
| 5,776,561 A | 7/1998 | Lindauer et al. |
| 5,805,768 A | 9/1998 | Schwartz et al. |
| 5,810,201 A | 9/1998 | Besse et al. |
| 5,816,446 A | 10/1998 | Steindorf et al. |
| 5,832,320 A | 11/1998 | Wittek |
| 5,881,714 A | 3/1999 | Yokoi et al. |
| 5,884,808 A | 3/1999 | Muderlak et al. |
| 5,887,118 A | 3/1999 | Huffman et al. |
| 5,894,841 A | 4/1999 | Voges |
| 5,898,475 A | 4/1999 | Martin |
| 5,899,381 A | 5/1999 | Gordon et al. |
| 5,899,382 A | 5/1999 | Hayes et al. |
| 5,908,231 A | 6/1999 | Huff |
| 5,924,597 A | 7/1999 | Lynn |
| 5,938,117 A | 8/1999 | Ivri |
| 5,949,522 A | 9/1999 | Manne |
| 5,972,290 A | 10/1999 | De Sousa |
| 5,975,675 A | 11/1999 | Kim |
| 6,000,658 A | 12/1999 | McCall, Jr. |
| 6,003,727 A | 12/1999 | Marshall |
| 6,013,231 A | 1/2000 | Zaunbrecher et al. |
| 6,039,212 A | 3/2000 | Singh |
| 6,044,202 A | 3/2000 | Junkel |
| 6,053,738 A | 4/2000 | Ivey, Jr. |
| 6,123,935 A | 9/2000 | Wefler et al. |
| 6,136,277 A | 10/2000 | Nardini |
| 6,189,810 B1 | 2/2001 | Nerushai et al. |
| 6,196,218 B1 | 3/2001 | Voges |
| 6,231,032 B1 | 5/2001 | Ivey, Jr. |
| 6,234,455 B1 | 5/2001 | Wittek |
| 6,241,944 B1 | 6/2001 | Budman |
| 6,254,065 B1 | 7/2001 | Ehrensperger et al. |
| 6,254,248 B1 | 7/2001 | McAuley et al. |
| 6,279,836 B1 | 8/2001 | Toetschinger et al. |
| 6,293,474 B1 | 9/2001 | Helf et al. |
| 6,296,196 B1 | 10/2001 | Denen et al. |
| D451,990 S | 12/2001 | Millet |
| 6,328,287 B2 | 12/2001 | Wittek |

| | | | | | | |
|---|---|---|---|---|---|---|
| 6,338,818 B2 | 1/2002 | Budman | | 2002/0158351 A1 | 10/2002 | Wohrle |
| 6,341,732 B1 | 1/2002 | Martin et al. | | 2003/0006303 A1 | 1/2003 | Ivey et al. |
| 6,357,726 B1 | 3/2002 | Watkins | | 2003/0102384 A1 | 6/2003 | Walter et al. |
| 6,371,451 B1 | 4/2002 | Choi | | 2003/0107139 A1 | 6/2003 | Wohrle |
| 6,382,522 B2 | 5/2002 | Tomkins et al. | | 2003/0138241 A1 | 7/2003 | Pedrotti et al. |
| 6,390,453 B1 | 5/2002 | Frederickson et al. | | 2003/0164557 A1 | 9/2003 | Cheng et al. |
| 6,406,004 B1 | 6/2002 | Ude | | 2003/0168524 A1 | 9/2003 | Hess et al. |
| 6,409,093 B2 | 6/2002 | Ulczynski et al. | | 2003/0168751 A1 | 9/2003 | Bartsch et al. |
| 6,421,944 B1 | 7/2002 | Budman | | 2003/0175148 A1 | 9/2003 | Kvietok et al. |
| 6,439,474 B2 | 8/2002 | Denen | | 2003/0192959 A1 | 10/2003 | Hess et al. |
| D463,437 S | 9/2002 | Bush et al. | | 2003/0206834 A1 | 11/2003 | Chiao et al. |
| 6,446,583 B2 | 9/2002 | Vieira | | 2004/0007787 A1 | 1/2004 | Kvietok et al. |
| 6,448,219 B1 | 9/2002 | Cooper | | 2004/0009103 A1 | 1/2004 | Westring |
| 6,450,419 B1 | 9/2002 | Martens, III et al. | | 2004/0016818 A1 | 1/2004 | Murdell et al. |
| D464,130 S | 10/2002 | Denham et al. | | 2004/0028551 A1 | 2/2004 | Kvietok et al. |
| 6,487,367 B2 | 11/2002 | Vieira | | 2004/0033067 A1 | 2/2004 | He et al. |
| 6,501,906 B2 | 12/2002 | Vieira | | 2004/0033171 A1 | 2/2004 | Kvietok et al. |
| 6,502,762 B2 | 1/2003 | Tuttobene, Jr. | | 2004/0071456 A1 | 4/2004 | Levine et al. |
| 6,505,759 B2 | 1/2003 | Holyfield | | 2004/0131509 A1 | 7/2004 | He et al. |
| 6,511,531 B1 | 1/2003 | Cartellone | | 2004/0195372 A1 | 10/2004 | Yoshikawa et al. |
| 6,520,826 B2 | 2/2003 | Spector | | 2004/0217188 A1 | 11/2004 | McEwen |
| 6,533,193 B2 | 3/2003 | White | | 2004/0217197 A1 | 11/2004 | Mazooji et al. |
| 6,536,746 B2 | 3/2003 | Watkins | | 2004/0223871 A1 | 11/2004 | Woo et al. |
| 6,542,442 B2 | 4/2003 | Kaslon | | 2004/0223891 A1 | 11/2004 | Brown |
| 6,554,203 B2 | 4/2003 | Hess et al. | | 2004/0223943 A1 | 11/2004 | Woo et al. |
| 6,556,272 B1 | 4/2003 | Du et al. | | 2004/0241053 A1 | 12/2004 | Thompson et al. |
| 6,563,091 B2 | 5/2003 | Vieira | | 2004/0247301 A1 | 12/2004 | Yip et al. |
| 6,568,659 B2 | 5/2003 | Hugon | | 2004/0265164 A1 | 12/2004 | Woo et al. |
| 6,569,387 B1 | 5/2003 | Furner et al. | | 2005/0001337 A1 | 1/2005 | Pankhurst et al. |
| 6,581,915 B2 | 6/2003 | Bartsch et al. | | 2005/0028819 A1 | 2/2005 | Manne |
| 6,584,633 B2 | 7/2003 | Chute et al. | | 2005/0147523 A1 | 7/2005 | Laudamiel-Pellet et al. |
| 6,592,104 B2 | 7/2003 | Cox | | 2005/0147539 A1 | 7/2005 | Laudamiel-Pellet et al. |
| 6,602,475 B1 | 8/2003 | Chiao | | 2005/0161522 A1 | 7/2005 | Kvietok et al. |
| 6,603,924 B2 | 8/2003 | Brown et al. | | 2005/0201944 A1 | 9/2005 | Kvietok et al. |
| 6,610,254 B1 | 8/2003 | Furner et al. | | 2005/0211790 A1 | 9/2005 | Kvietok et al. |
| 6,619,559 B2 | 9/2003 | Wohrle | | 2005/0214158 A1 | 9/2005 | Kvietok et al. |
| 6,654,664 B1 | 11/2003 | Chiao | | 2006/0018786 A1 | 1/2006 | Tolman et al. |
| 6,661,967 B2 | 12/2003 | Levine et al. | | 2006/0018803 A1 | 1/2006 | Kvietok et al. |
| 6,706,988 B1 | 3/2004 | Helf et al. | | 2006/0067859 A1 * | 3/2006 | Laudamiel-Pellet et al. . 422/123 |
| 6,712,287 B1 | 3/2004 | Le Pesant et al. | | 2006/0097065 A1 | 5/2006 | Kvietok et al. |
| 6,713,024 B1 | 3/2004 | Arnell et al. | | 2006/0097066 A1 | 5/2006 | Kvietok et al. |
| 6,714,725 B2 | 3/2004 | Grone et al. | | 2006/0193611 A1 | 8/2006 | Ballesteros et al. |
| 6,728,478 B2 | 4/2004 | Cox et al. | | | | |
| 6,769,905 B2 | 8/2004 | Gray et al. | | FOREIGN PATENT DOCUMENTS | | |
| 6,783,117 B2 | 8/2004 | Wohrle | | EP | 295 129 | 12/1988 |
| 6,790,011 B1 | 9/2004 | Le Pesant et al. | | EP | 1 247 446 | 10/2002 |
| 6,790,408 B2 | 9/2004 | Whitby et al. | | EP | 1 247 447 | 10/2002 |
| 6,792,199 B2 | 9/2004 | Levine et al. | | EP | 1 303 316 | 4/2003 |
| 6,793,149 B2 | 9/2004 | Schramm et al. | | EP | 1 303 317 | 4/2003 |
| D497,288 S | 10/2004 | McGuyer | | EP | 1 303 318 | 4/2003 |
| 6,802,460 B2 | 10/2004 | Hess et al. | | EP | 1 303 319 | 4/2003 |
| 6,803,987 B2 | 10/2004 | Manne | | EP | 1 469 131 | 10/2004 |
| 6,810,204 B2 | 10/2004 | Grone et al. | | GB | 2 253 732 | 9/1992 |
| 6,834,847 B2 | 12/2004 | Bartsch et al. | | GB | 2 401 047 | 11/2004 |
| 6,842,218 B1 | 1/2005 | Manne | | GB | 2 401 790 | 11/2004 |
| 6,843,430 B2 | 1/2005 | Boticki et al. | | GB | 2 418 859 | 4/2006 |
| 6,859,615 B2 | 2/2005 | Yip et al. | | JP | 04024029 | 1/1992 |
| 6,871,794 B2 | 3/2005 | McEwen | | JP | 404267740 | 9/1992 |
| 6,896,196 B2 | 5/2005 | Vieira | | JP | 404354950 | 12/1992 |
| 6,912,355 B2 | 6/2005 | Vieira | | JP | 06 320083 | 11/1994 |
| 6,913,208 B2 | 7/2005 | Tabata et al. | | JP | 408336578 | 12/1996 |
| 6,913,733 B2 | 7/2005 | Hardy et al. | | JP | 11-000391 | 1/1999 |
| 6,921,024 B2 | 7/2005 | Donnelly et al. | | WO | WO 00/12143 | 3/2000 |
| 7,011,795 B2 | 3/2006 | Thompson et al. | | WO | WO 00/53301 | 9/2000 |
| 7,021,494 B2 | 4/2006 | Mazooji et al. | | WO | WO 00/60486 | 10/2000 |
| 7,223,166 B1 | 5/2007 | Wiseman, Sr. et al. | | WO | WO 00/60489 | 10/2000 |
| 2001/0048037 A1 | 12/2001 | Bell et al. | | WO | 0204055 A | 1/2002 |
| 2002/0018181 A1 | 2/2002 | Manne | | WO | WO 02/09772 | 2/2002 |
| 2002/0036358 A1 | 3/2002 | Watkins | | WO | WO 02/09773 | 2/2002 |
| 2002/0066798 A1 | 6/2002 | Laudamiel-Pellet et al. | | WO | WO 02/09776 | 2/2002 |
| 2002/0068009 A1 | 6/2002 | Laudamiel-Pellet et al. | | WO | WO 02/09779 | 2/2002 |
| 2002/0068010 A1 | 6/2002 | Laudamiel-Pellet et al. | | WO | WO 02/32472 | 4/2002 |
| 2002/0114744 A1 | 8/2002 | Chiao et al. | | | | |

| | | |
|---|---|---|
| WO | WO 03/068412 | 8/2003 |
| WO | WO 03/098971 | 11/2003 |
| WO | WO 03/099458 | 12/2003 |
| WO | WO 03/102291 | 12/2003 |
| WO | WO 03/105652 | 12/2003 |
| WO | WO 2004/007008 | 1/2004 |
| WO | WO 2004/009142 | 1/2004 |
| WO | WO 2004/011836 | 2/2004 |
| WO | WO 2004/043502 | 5/2004 |
| WO | WO 2004/071935 | 8/2004 |
| WO | WO 2004/093927 | 11/2004 |
| WO | WO 2004/093928 | 11/2004 |
| WO | WO 2004/093929 | 11/2004 |
| WO | WO 2004/105813 | 12/2004 |
| WO | WO 2004/105814 | 12/2004 |
| WO | WO 2004/105815 | 12/2004 |
| WO | WO 2004/105878 | 12/2004 |
| WO | WO 2005/011761 | 2/2005 |
| WO | 2006004891 A | 1/2006 |
| WO | WO 2006/105347 | 10/2007 |

OTHER PUBLICATIONS

SCJ Create a Scent web page http://www.glade.com/glade-plug-ins/, 3 pages, printed May 16, 2007.

* cited by examiner

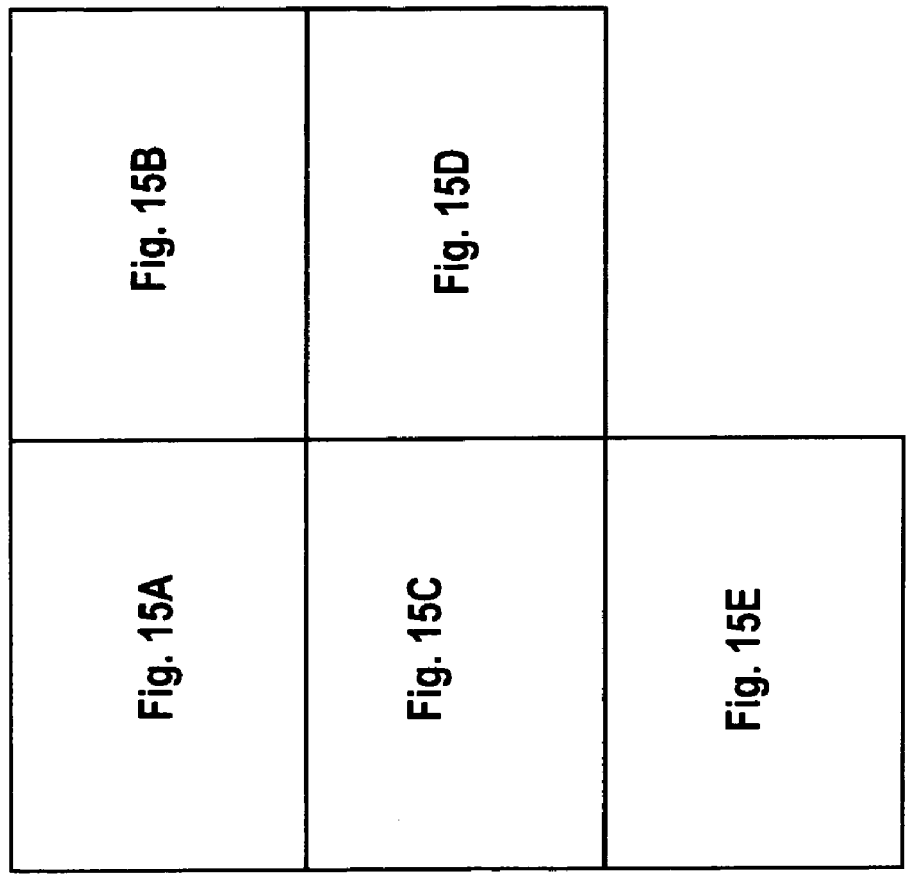

APPARATUS FOR AND METHOD OF DISPENSING ACTIVE MATERIALS

CROSS REFERENCE TO RELATED APPLICATIONS

This application is a continuation-in-part of U.S. application Ser. No. 11/403,166, filed Apr. 12, 2006, entitled "Diffusion Device," which claims the benefit of U.S. Provisional Application No. 60/670,519, filed Apr. 12, 2005.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Technical Field

The present invention relates to dispensing of active materials, and more particularly, to apparatuses for and methods of emitting more than one active material.

2. Description of the Background of the Invention

A multitude of active material diffusion devices or diffusers exist in the marketplace. Many of such devices are passive devices that require only ambient air flow to disperse the liquid active material therein. Other devices are battery-powered or receive household power via a cord and plug extending from the device.

Various means for dispensing active materials from diffusion devices are also known in the art. For example, some diffusion devices include a heating element for heating an active material to promote vaporization thereof. Other diffusion devices employ a fan or blower to generate air flow to direct active material out of the diffusion device into the surrounding environment. In another type of diffusion device, active material may be emitted from the device using a bolus generator that delivers a pulse of air to eject a scent ring. Still other diffusion devices dispense active materials utilize ultrasonic means to dispense active materials therefrom.

In one example a diffusion device includes two heaters for dispersion of fragrances. The device includes a housing, a plug extending from the housing for insertion into an outlet, and two containers having fragrances therein and wicks extending therefrom to absorb fragrances from the containers. Each of the heaters is disposed adjacent one of the wicks to heat the respective wick to vaporize the fragrances therein. Optionally, a CPU controlled by internal software may first activate a first of the two heaters for a predetermined period of time. After the period of time expires, the CPU deactivates the first heater and thereafter activates the second heater.

Other diffusion devices include a housing having a cavity for receiving a cartridge. The cartridge generally has a plurality of scent elements disposed on a rotatable disk. A blower is mounted in the housing to generate airflow by passing air across a scent element and out an aperture in the housing. The housing further includes rotating means that rotate the rotatable disk, thereby rotating the scent elements thereon. The device diffuses a first scent for a predetermined time period and thereafter rotates the disk to a second scent and diffuses the second scent for the predetermined time period. This process repeats itself until the last scent element is diffused for the time period and then the disk is rotated to a home position.

Piezoelectrically actuated vibratory type liquid atomization apparatuses are described in Helf et al. U.S. Pat. No. 6,293,474, Martin et al. U.S. Pat. No. 6,341,732, Tomkins et al. U.S. Pat. No. 6,382,522, Martens, III et al. U.S. Pat. No. 6,450,419, Boticki et al. U.S. Pat. No. 6,843,4130, all of which are assigned to the assignee of the present application and which are hereby incorporated by reference herein. These patents describe a piezoelectrically actuated vibratory type liquid atomization apparatus comprising a piezoelectric actuating element coupled to a liquid atomization plate. The piezoelectric actuating element vibrates the liquid atomization plate in response to alternating electrical voltages applied to the actuating element. The vibration of the plate causes atomization of a liquid supplied to it by a liquid delivery system. An electrical circuit is provided to supply the alternating electrical voltages to conductive elements that are in electrical contract with opposite sides of the actuating element. The conductive elements may also serve to support the actuating elements and the liquid atomization plate in a housing that contains the device.

SUMMARY OF THE INVENTION

According to one aspect of the present invention, an apparatus for dispensing active materials comprises a housing and control circuitry disposed within the housing. The control circuitry implements programming for a mode of operation in which during a first period of time a first active material is emitted, during a second period of time the first active material and a second active material are emitted, and during a third period of time the second active material is emitted, wherein during the second period of time, the first and second fragrances alternated.

According to yet another aspect of the present invention, a method of dispensing active materials comprises the step of emitting a first active material for a first period of time. The method further includes the step of emitting the first active material and a second active material for a second period of time, wherein the first and second active material are alternated during the second period of time. Still further, the method includes the step of emitting the second active material for a third period of time.

According to another aspect of the present invention, a method of dispensing active materials comprises the step of periodically emitting discrete bursts of a first active material for a first period of time. The method further includes the steps of periodically emitting discrete bursts of the first active material and a second active material for a second period of time and periodically emitting discrete bursts of the second active material for a third period of time. During the second period of time, the first and second active materials are alternately emitted.

Other aspects and advantages of the device of the present invention will become apparent upon of the following detailed description.

DETAILED DESCRIPTION OF THE PREFERRED EMBODIMENTS

Figure 1:
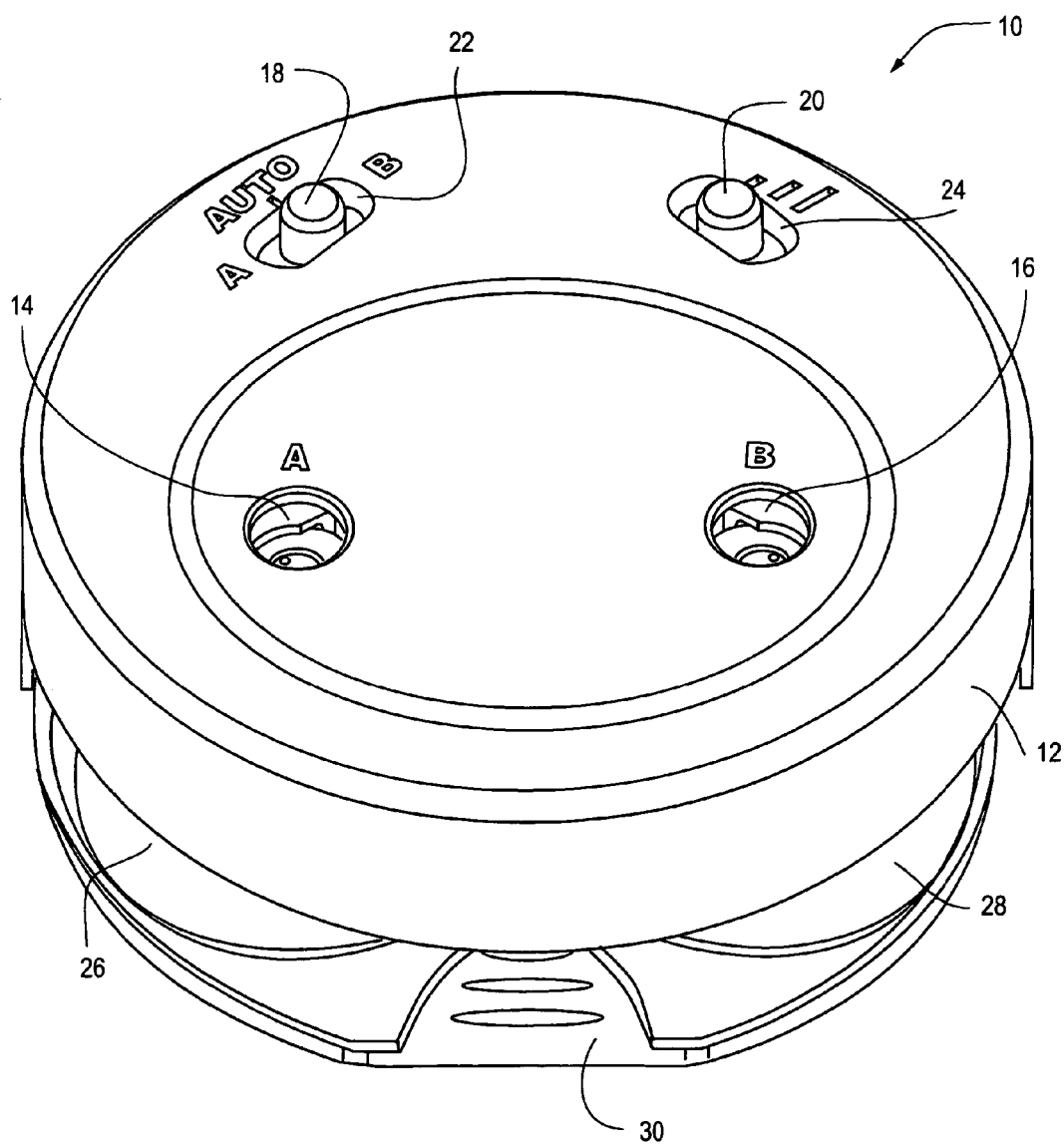
FIG. 1 is a top perspective view of a diffusion device.
Figure 2:
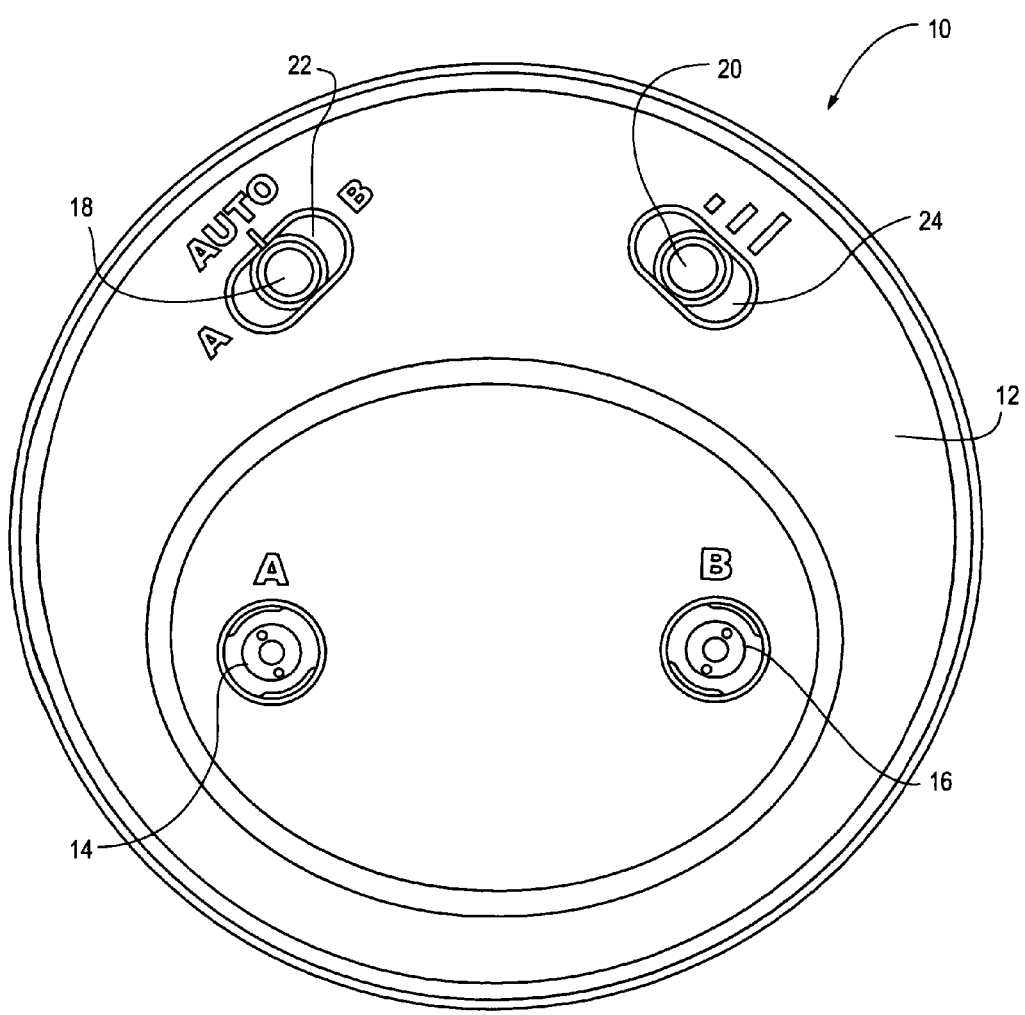
FIG. 2 is a plan view of the diffusion device of FIG. 1.
Figure 3:
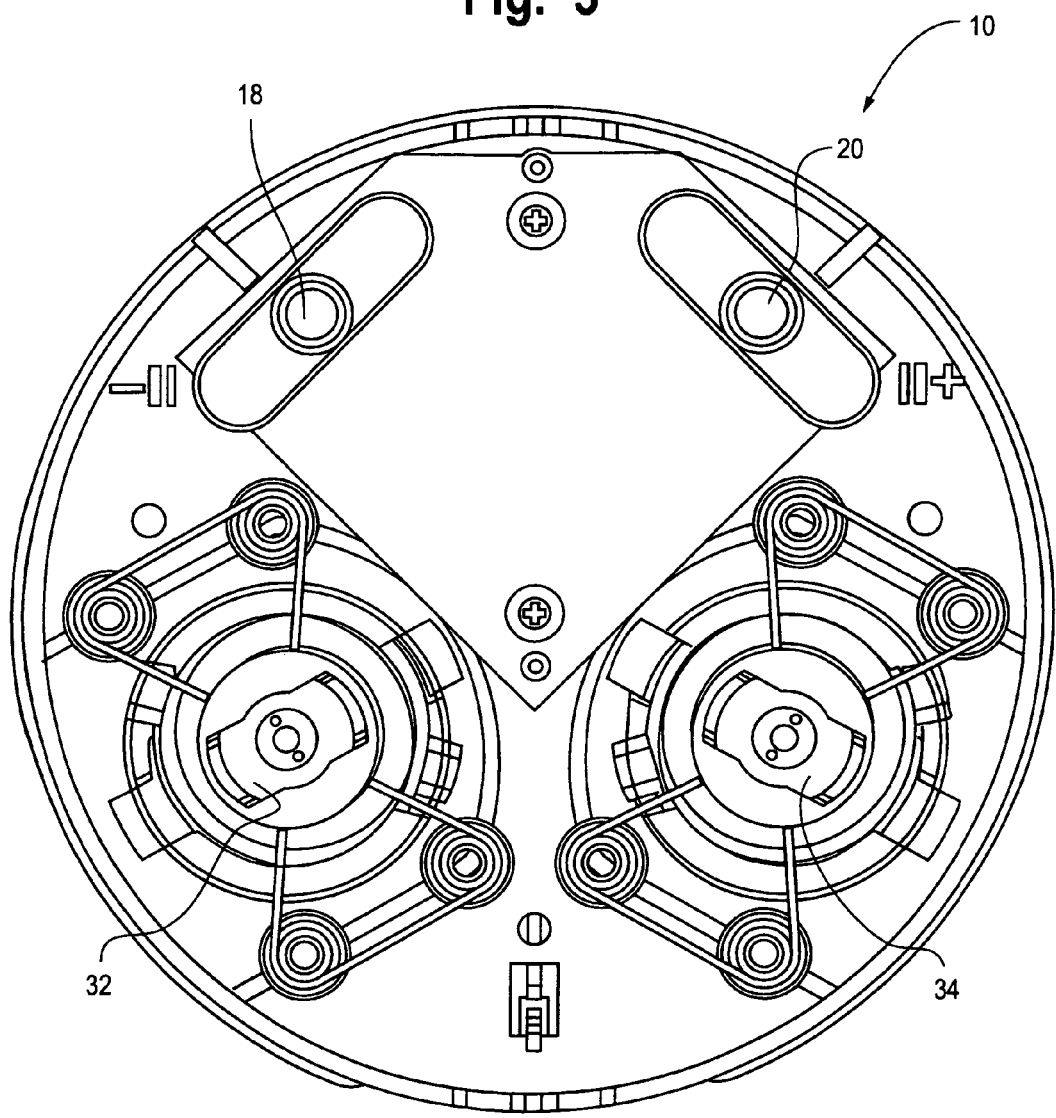
FIG. 3 is a plane view similar to that of FIG. 2 in which the housing is removed.

As seen in FIG. 1, a diffusion device 10 includes a cylindrical housing 12. The housing 12 includes two apertures 14 and 16 through which an aerosol active material may be emitted. Two multi-position switches 18 and 20 are disposed within housing 12. An operating mode switch 18 controls the operating mode of diffusion device 10 and extends through another aperture, 22 in the housing 12. An emission frequency switch 20 controls the emission frequency of diffusion device 10 and extends through yet another aperture 24 in the housing 12.

A container 26 containing an active material and having a wick extending therefrom is disposed within the housing 12 and an opening (not shown) of the container 26 is adjacent the aperture 14. An additional container 28, also containing an active material, which may be the same or different than the active material in the container 26, and having a wick extending therefrom, is disposed within the housing 12 and an opening (not shown) of the container 28 is disposed adjacent the aperture 16. The containers 26 and 28 are replaceable.

Illustratively, the types of liquid active materials described herein may be, for example, an insecticide, an insect repellant, an insect attractant, a disinfectant, a mold or mildew inhibitor, a fragrance, a disinfectant, an air purifier, an aromatherapy scent, an antiseptic, an odor eliminator, a positive fragrancing active material, an air-freshner, a deoderizer, or the like, and combinations thereof. The present invention contemplates the use of the same or different active materials and/or the same or different types of active materials. For example, both of the containers 26 and 28 may include a lavender fragrance therein. Alternatively, the container 26 may include a strawberry fragrance and the container 28 may include a vanilla fragrance. Still alternatively, the container 26 may include an insect repellant and the container 28 may include an odor eliminator. As such, any combination of types of liquid active materials may be utilized in the containers 26, 28.

A bottom cover 30 is connected to the housing 12 and provides a planar bottom surface for the diffusion device 10. Both the housing 12 and the bottom cover 30 may be made of a thermoplastic material and may be injection molded, although the housing 12 and the bottom cover 30 may be made of any other suitable material.

FIGS. 2 and 3 depict top views of the diffusion device 10, wherein like reference numerals throughout the drawings designate like structures. FIG. 3 is similar to FIG. 2 except that the housing 12 has been omitted in FIG. 3. The operating mode switch 18 and the emission frequency switch 20 are shown in FIG. 3, as are the piezoelectric devices 32 and 34. The use of piezoelectric devices to atomize liquids is well known; and examples of such devices are described in Martens, III et al. U.S. Pat. No. 6,450,419, Helf et al. U.S. Pat. No. 6,706,988, and Boticki et al. U.S. Pat. No. 6,843,430 incorporated by reference herein. In general, these devices apply an alternating voltage to a piezoelectric element to cause the element to expand and contrast. The piezoelectric element is coupled to a perforated orifice plate, which in turn is in surface tension contact with a liquid source. The expansion and contraction of the piezoelectric element causes the orifice plate to vibrate up and down whereupon liquid is driven through the perforations and is then emitted upwardly in the form of aerosolized particles.

The piezoelectric device 32 is located within the housing 12 between the container 26 and the aperture 14 and works as described above to atomize the active material of the container 26. Similarly, the piezoelectric device 34 is located within the housing 12 between the container 28 and the aperture 16 within the housing 12 and also works as described above to atomize the active material of the container 28.

The operating mode switch 18 controls the mode of operation of the diffusion device 10. For example, in one embodiment, the operating mode switch 18 may be a slide switch with three different positions. When a user slides the switch 18 to a first position, a mode "A" of operation may be initiated wherein a first active material is emitted continuously at a selected intensity level. When the user slides the switch 18 to a second position, a mode "B" of operation may be entered herein a second active material is emitted continuously at a selected intensity level. When the switch 18 is moved to a third position, an "auto" mode of operation may be initiated wherein the diffusion device 10 alternates between emitting the first active material and the second active material. Illustratively, in the third mode, the first active material may be emitted for a predetermined period of time and, when the predetermined period of time has expired, the second active material may be emitted for a predetermined period of time that may or not be the same as that of the first active material. The predetermined periods may be any preferred periods of time, but preferably are between about one minute and about twenty-four hours. In one preferred embodiment, the predetermined period is three hours. In another preferred embodiment, the predetermined period is twenty-four hours. In yet another preferred embodiment, the predetermined period is sixty minutes. Still further, in another preferred embodiment, the predetermined period is ninety minutes.

Optionally, additional and/or substitute modes of operation may be used with the device 10 of the present invention. Such modes of operation may be implemented by the circuitry disclosed herein with or without changes to the physical parts, construction, and/or circuit element arrangements, it being understood that such mode(s) can be implemented by software and/or hardware changes, as desired. Illustratively, one mode varies the output of the active material(s) from the diffusion device 10. For example, the output may be varied by gradually increasing or decreasing the amount of active material emitted by the device. Optionally, the amount of active material may be increased to a higher amount or level of active material and may remain at that level for a predetermined period of time. The predetermined period of time may be any time limit that prevents habituation of the active material, such as any time period between one minute and thirty minutes. After the predetermined period of time, the amount of active material emitted may be decreased to a lower level and may remain at that level for the same or a different predetermined period of time. This cycle may be repeated continuously or may be repeated in a random or complex pattern. Also, any number of different active material emission levels may be utilized in such a mode of operation.

In another mode of operation, emission of active material may be discontinued for a predetermined period of time. The predetermined period of time may be any period of time that allows the active material level to decrease or partially or fully dissipate from the surrounding environment, but preferably the predetermined time period is between about one minute and about thirty minutes. After the predetermined time has expired, the emission of active material is resumed. This cycle may be repeated with the same, increasing, or decreasing periods of time. Still alternatively, in another mode of operation, two or more active materials may be disposed simultaneously.

Figure 4:
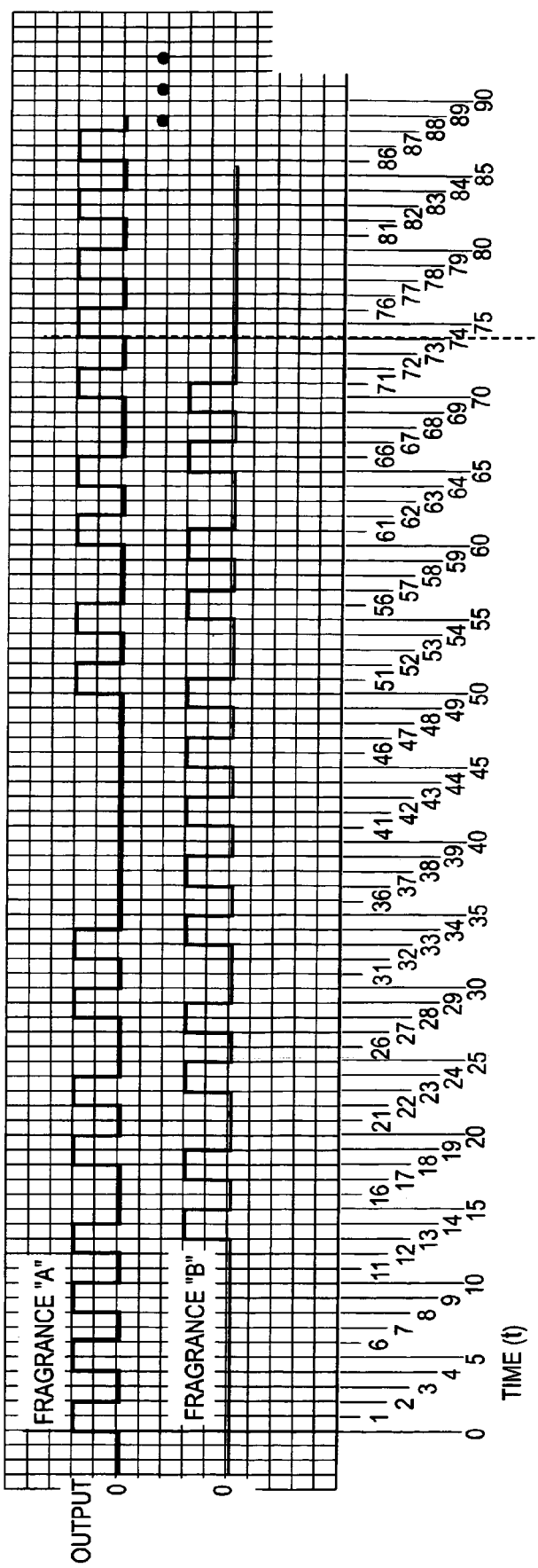
FIG. 4 is a diagrammatic representation of an embodiment of a mode of operation for a diffusion device such as the diffusion device of FIG. 1.
Figure 5:
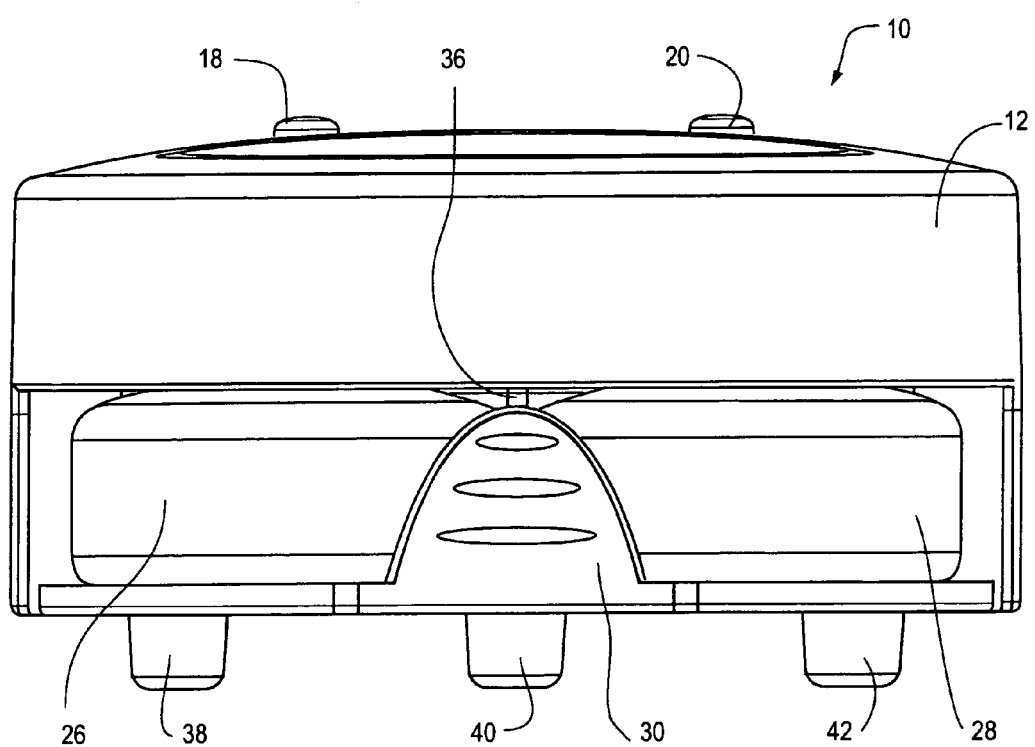
FIG. 5 is a front elevational view of the diffusion device of FIG. 1.
Figure 6:
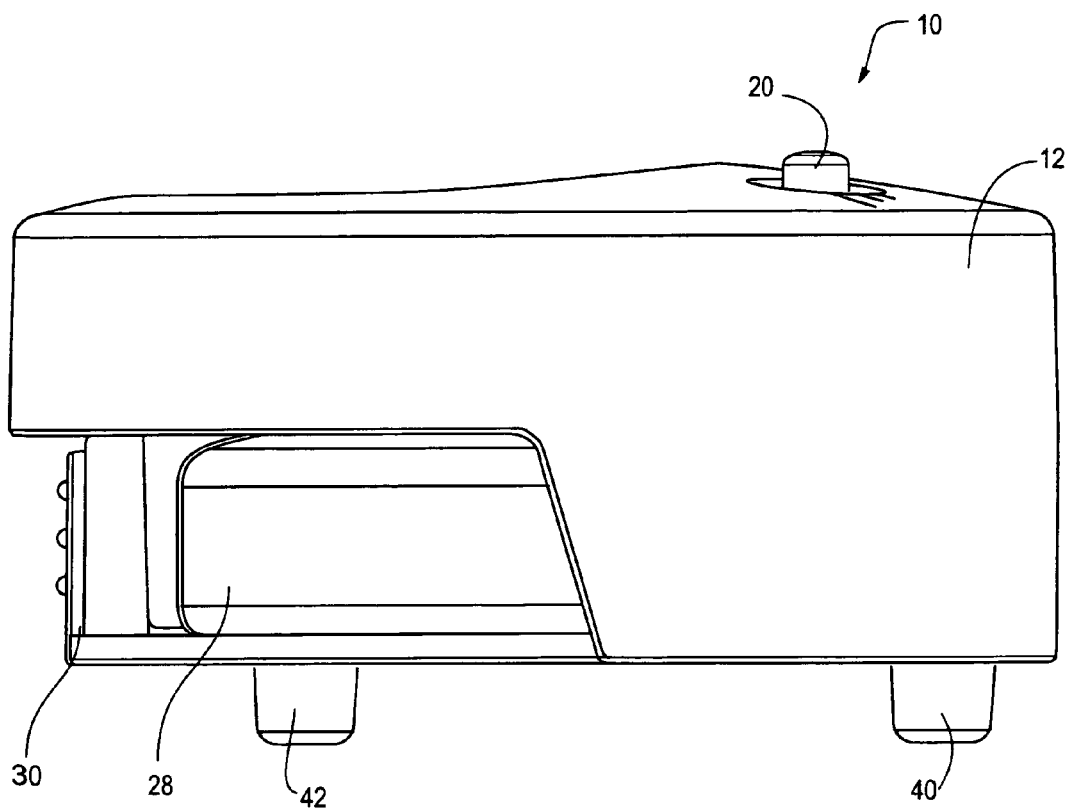
FIG. 6 is an elevational view of a first side of the diffusion device of FIG. 1.
Figure 7:
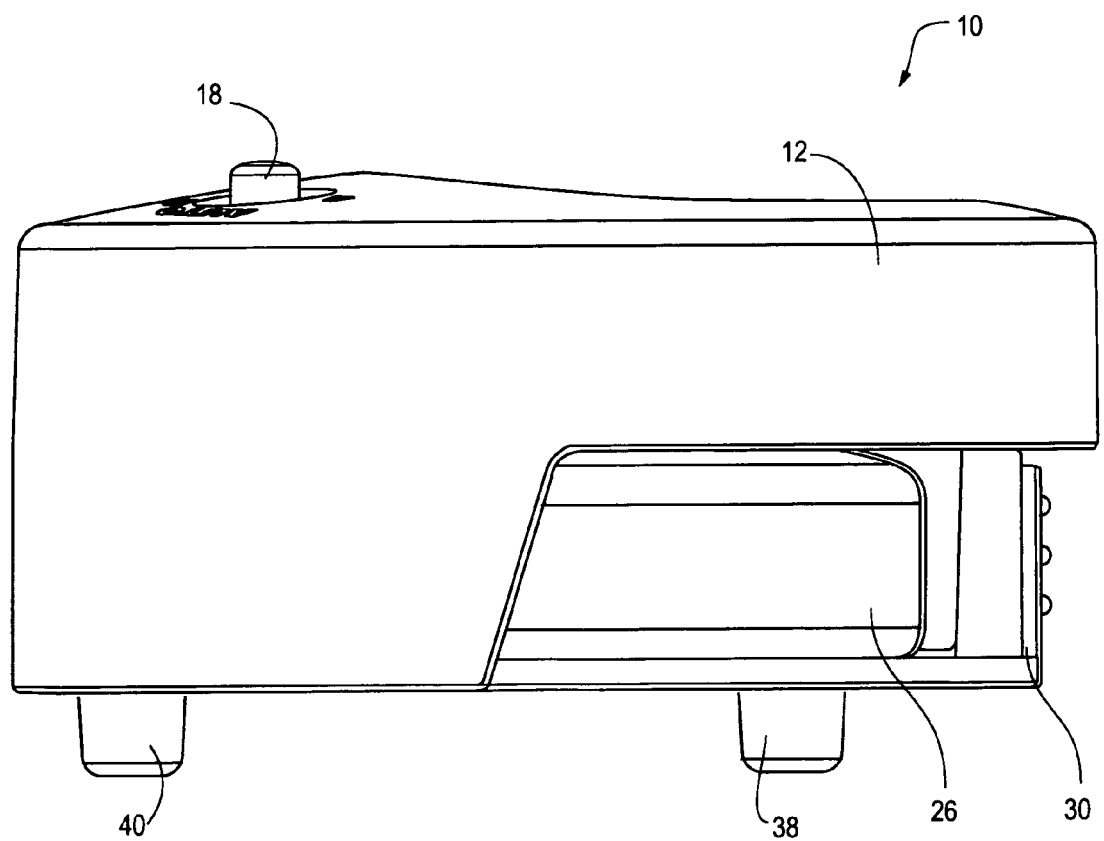
FIG. 7 is an elevational view of a second side of the diffusion device of FIG. 1.
Figure 8:
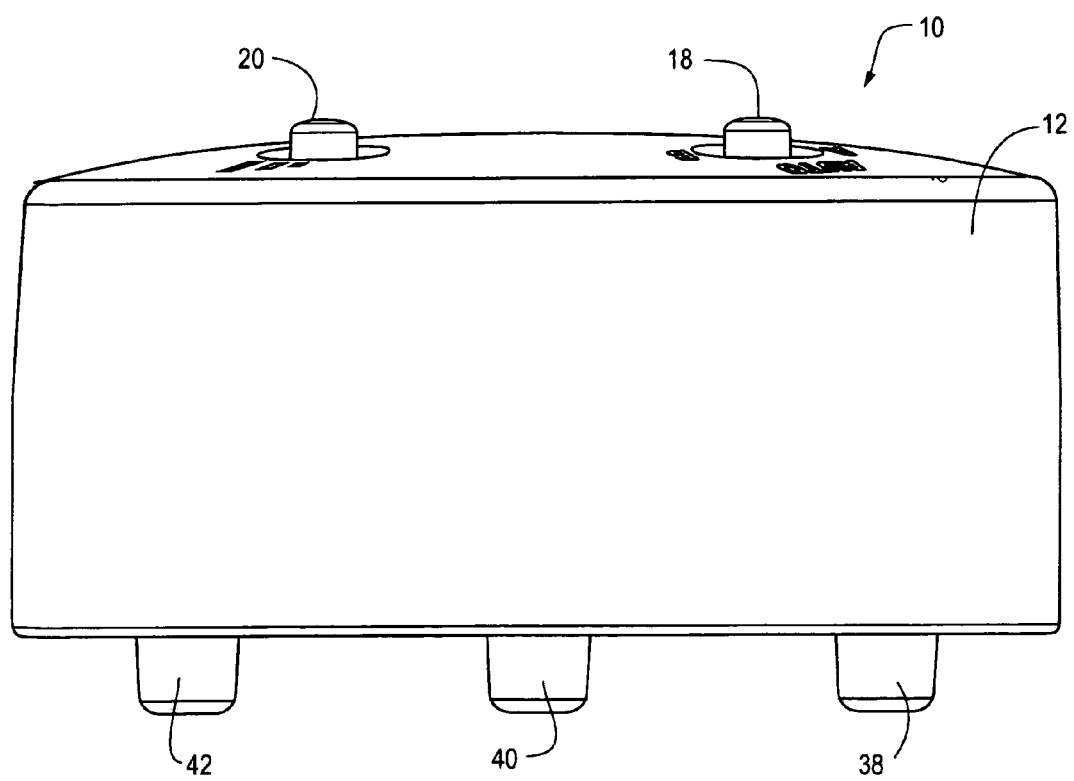
FIG. 8 is back elevational view of the diffusion device of FIG. 1.

In another embodiment, when the "auto" mode of operation is selected, the emission of first and second fragrances A and B, respectively, may be undertaken as seen in FIG. 4, An overall sequence for the mode of operation of FIG. 4 is represented between times $t_0$ and $t_{74}$, wherein the overall sequence is repeated to automatically alternate emission of fragrances A and B.

The first fragrance A may be purified or periodically dispensed in the form of discrete emissions or bursts into the surrounding atmosphere for a first period of time. In particular, periodic puffs of fragrance A are represented in the diagram of FIG. 4 by high-state portions of a control waveform for the piezoelectric devices 32, 34 between times $t_0$ and $t_2$, $t_4$ and $t_6$, and $t_8$ and $t_{10}$. Each periodic puff of fragrance A is followed by a dwell period (i.e., a period representing a duration between puffs in which the diffusion device 10 is inactive). The dwell periods are represented in the diagram of FIG. 4 by low-state portions of the control waveform for the piezoelectric devices 32, 34 between times $t_2$ and $t_4$, $t_6$ and $t_8$, and $t_{10}$ and $t_{12}$. The first period of time is preferably between about 5 minutes and about 7 days, more preferably between about 2 hours and about 24 hours, and most preferably about 12 hours.

Before emission of fragrance A is terminated, the first fragrance A and a second fragrance B are both emitted for a second time period. During the second time period, a first sequence is repeated to alternate fragrances A and B, wherein the first sequence includes a puff of fragrance A, as seen between times $t_{12}$ and $t_{14}$ in FIG. 4. Before the puff of fragrance A is terminated, a puff of fragrance B is initiated and is emitted from a time $t_{13}$ until a time $t_{15}$, thereby creating a first overlap period of time between $t_{13}$ and $t_{14}$ in which fragrances A and B are both emitted. The first overlap period of time preferably has a duration between about 1 millisecond and about 5 seconds, more preferably between about 3 milliseconds and about 1 seconds, and most preferably about 5.5 milliseconds. The first sequence further includes fragrance A entering a dwell period at a time $t_{14}$ until a time $t_{18}$ and fragrance B entering a dwell period at a time $t_{15}$ until a time $t_{17}$. Another puff of fragrance B is emitted between times $t_{17}$ and $t_{19}$, but before emission of fragrance B is concluded, a puff of fragrance A is initiated at a time $t_{18}$ and continues until a time $t_{20}$, wherein a second overlap period occurs between times $t_{18}$ and $t_{19}$. Preferably, although not necessarily, the second overlap period has a duration that is the same as or similar to that of the first overlap period. Fragrance B enters a dwell period at time $t_{19}$ and thereafter, fragrance A enters a dwell period at a time $t_{20}$. At a time $t_{22}$, fragrance A is again puffed and the first sequence is repeated. The first sequence may be repeated any number of times, but is preferably repeated enough times to attain a preferred period of time for the second time period, discussed in detail below. After repetition of the first sequence, fragrance A is again puffed, for example between times $t_{32}$ and $t_{34}$. Before the puff of fragrance A is finished, a puff of fragrance B is initiated at a time $t_{33}$ and continues to a time $t_{35}$. Fragrance A enters a dwell period at the time $t_{34}$ and thereafter fragrance B enters a dwell period at a time $t_{35}$ extending to a time $t_{37}$, whereupon the second period of time in concluded. The second period of time is preferably between about 11 milliseconds and about 24 hours, more preferably between about 60 seconds and about 30 minutes, and most preferably about 15 minutes.

At a time $t_{37}$, fragrance B is puffed and periodically dispensed in discrete emissions or burst into the surrounding atmosphere for a third period of time. Periodic puffs of fragrance B during the third period of time are represented in the diagram of FIG. 4 by increases in output between times $t_{37}$ and $t_{39}$, $t_{41}$ and $t_{43}$, and $t_{45}$ and $t_{47}$. Each periodic puff of fragrance A is followed by a dwell period, wherein the dwell periods are represented in the diagram of FIG. 4 by terminations in the output between times $t_{39}$ and $t_{41}$, and $t_{43}$ and $t_{45}$, and $t_{47}$ and $t_{49}$. The third period of time is preferably between about 5 minutes and 7 days, more preferably between about 2 hours and about 24 hours, and most preferably about 12 hours.

The second fragrance B and the first fragrance A are both emitted for a fourth period of time before emission of fragrance B is terminated. During the fourth period of time, a second sequence is repeated, wherein the second sequence includes a puff of fragrance B between times $t_{49}$ and $t_{51}$ of FIG. 4. Before the puff of fragrance B is finished, a puff of fragrance A is initiated and emitted between time $t_{50}$ and $t_{52}$, thereby creating a second overlap period of time between times $t_{50}$ and $t_{51}$ in which fragrances A and B are emitted. Preferably, the second overlap period has a duration that is the same as or similar to that of the first overlap period duration, although the second overlap period may have a different duration from that of the first overlap period duration. The second sequence further includes fragrance B entering a dwell period at a time $t_{51}$ until a time $t_{55}$ and fragrance A entering a dwell period between times $t_{51}$ and $t_{54}$. At time $t_{54}$, another puff of fragrance A is emitted between times $t_{54}$ and $t_{56}$, but before of emission A is terminated, a puff of fragrance B is initiated at a time $t_{55}$ and extends until a time $t_{57}$. Fragrance A enters a dwell period at the time $t_{56}$ and thereafter, fragrance B enters a dwell period at the time $t_{57}$. At a time $t_{59}$, fragrance B is again puffed and the second sequence is preferably, although not necessarily, repeated. The second sequence is preferably, although not necessarily, repeated the same number of times as the first sequence. After the second sequence is carried out at least once, fragrance B is puffed between times $t_{69}$ and $t_{71}$ and, before the puff of fragrance B is concluded, a puff of fragrance A is initiated at a time $t_{70}$ and continues until a time $t_{72}$. Fragrance B enters a dwell period at the time $t_{71}$ and thereafter fragrance A enters a dwell period at the time $t_{72}$, thereby concluding the fourth period of time at a time $t_{74}$. The fourth period of time is preferably, although not necessarily, has the same duration as that of the second period of time.

At the time $t_{74}$, the overall sequence including the first, second, third, and fourth periods of time is preferably repeated as long as the diffusion device is in the "auto" mode of operation as depicted in FIG. 4. The overall sequence depicted in FIG. 4 may be implemented in electronic circuitry for any diffusion device emitting two fragrances. Additionally, the overall sequence in FIG. 4 may be altered to allow for emission of more than two fragrances.

Although the puff and dwell periods appear in FIG. 4 to have durations that are the same or similar to one another, the puff and dwell period durations need not be the same or similar to one another. Also, the puff periods need not all be the same duration and the dwell periods need not all be the same duration. In fact, the puff and/or dwell periods may increase or decrease in duration throughout the overall sequence. In a preferred embodiment, a duration of the dwell periods is greater than a duration of the puff periods. The duration of the puff periods is preferably between about 5 milliseconds and about 5 seconds, more preferably about 8 milliseconds and about 1 second, and most preferably about 11 milliseconds. The duration of the dwell periods is preferably between about 3 seconds and about 5 minutes, more preferably about 4 seconds and about 30 seconds, and most preferably about 5.5 seconds.

Any of the modes of operation has disclosed herein or as known in the art may be utilized alone or in any combination. Also, any of these modes of operation may be utilized with a diffusion device that emits a single active material or a diffusion device that emits multiple active materials.

The emission frequency switch 20 controls the frequency of active material emission of the diffusion device 10. For example, in one embodiment, the switch 20 may be a slide switch with three different positions. A first position may actuate a dwell period of a first predetermined period of time, wherein the dwell period represents a duration between sprays in which diffusion device 10 is inactive, i.e., not emitting active material. A second position may actuate a dwell period of a second predetermined period of time. A third position may actuate a dwell period of a third predetermined period of time. The predetermined time periods may be of preferred durations, but preferably are between a few seconds and a few minutes. Most preferably, the first, second, and third predetermined time periods are nine seconds, twelve seconds, and eighteen seconds, respectively.

Optionally, a slide switch with five different positions may be utilized, wherein the dwell periods may be similar to those of the slide switch with three different positions, but are preferably between a few seconds and a few minutes. Still optionally, the switches 18 and 20 may include any number of positions corresponding to a preferred number of modes or intensities.

Figure 9:
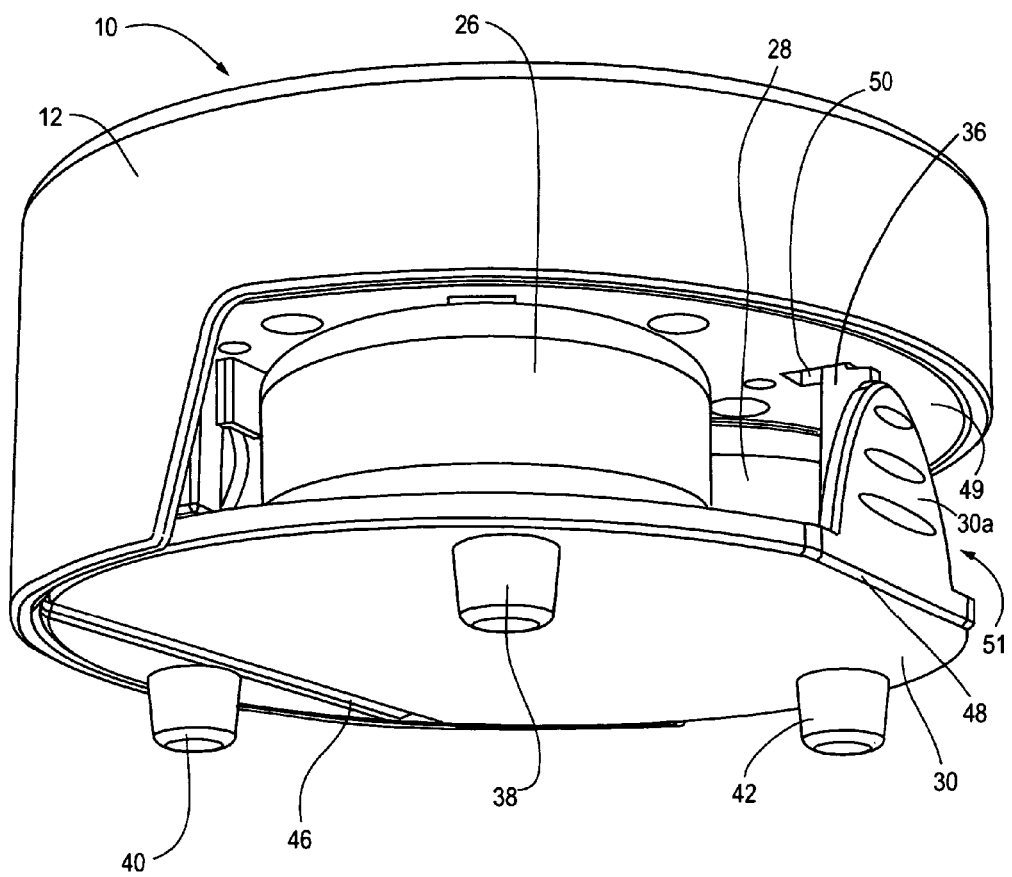
FIG. 9 is a bottom perspective view of the diffusion device of FIG. 1.

FIGS. 5-9 depict alternative views of the diffusion device 10, and further show the bottom cover 30 and optional legs 38, 40, and 42. Although three legs are depicted, and suitably number of legs that allow the device 10 to stand upright is possible. As shown in FIG. 9, the bottom cover 30 includes two hinged portions 46 and 48. The bottom cover 30 is attached to the housing 12 at a back side of the diffusion device by heat-staking or any other suitable fastening means, including, for example, rivets, press fit, snap fit, screws, ultrasonic welding, adhesives, or the like and combinations thereof. The optional legs 38, 40, and 42 may be attached to the bottom cover 30 in a similar fashion and may be made of a thermoplastic material or any other suitable material.

A flap portion 30a (FIG. 9), extending perpendicularly from the bottom cover 30 at the hinged portion 48 further includes a latch 36 for securing the bottom cover 30 to the housing 12. The latch 36 is adapted to engage a wall or surface 49 defining in part an aperture 50 within the housing 12 and may be flexibly released by pushing the flap portion 30a inward so that the latch 36 may moved out of interfering relationship with the wall or surface 49. The bottom cover 30 may then be lifted away from the housing 12 as it flexed at the hinged portion 46.

As seen in FIGS. 5-7 and 9, when the latch 36 is engaged with the aperture 50 in the wall 49, an opening 51 is formed between the bottom cover 30 and the wall 49. The opening 51 allows a user to determine a fluid level of the active materials in each of the containers 26, 28 without disengaging the latch 36 from the opening 51.

Figure 10:
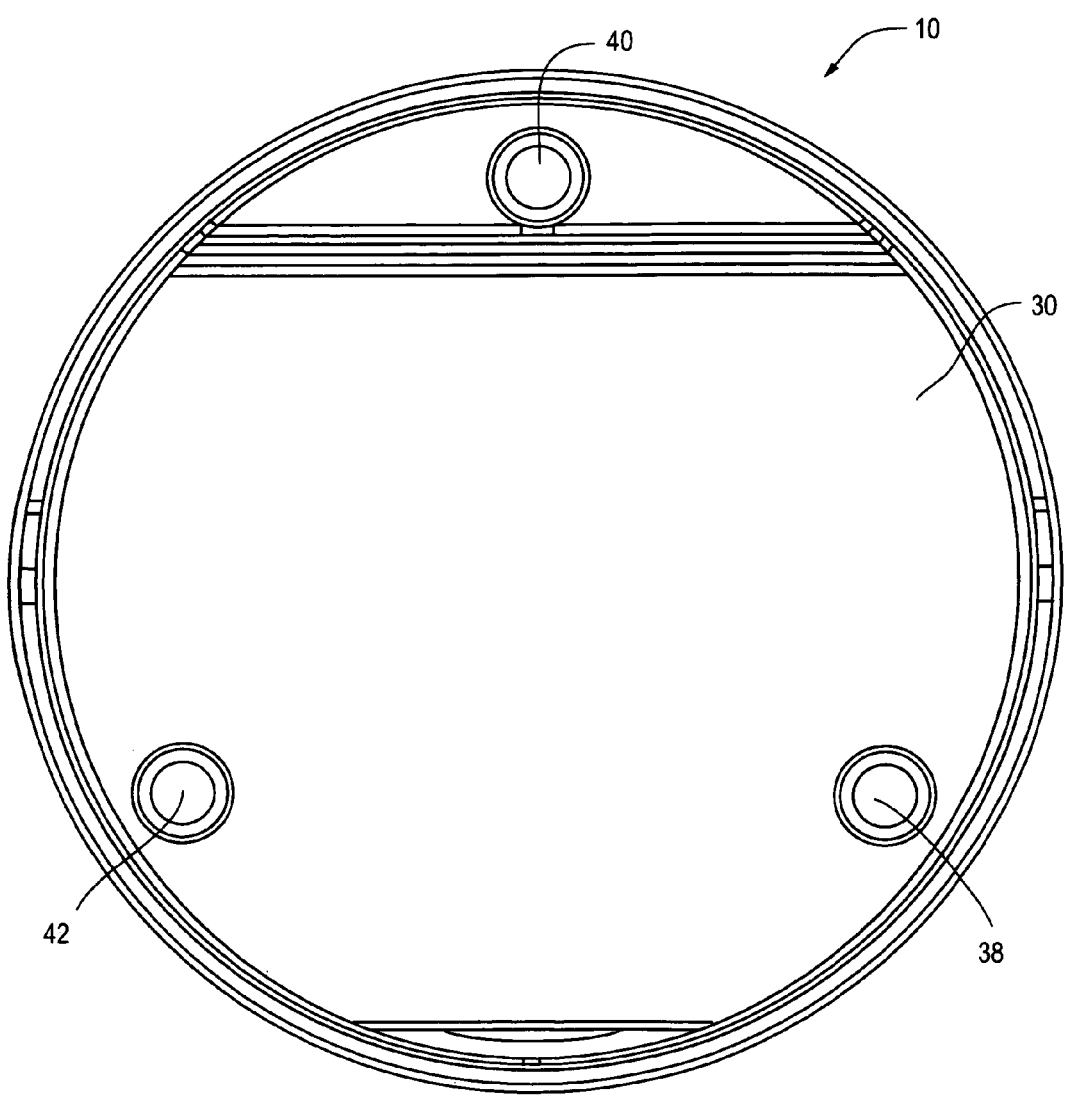
FIG. 10 is a bottom elevational plan view of the diffusion device of FIG. 1.
Figure 11:
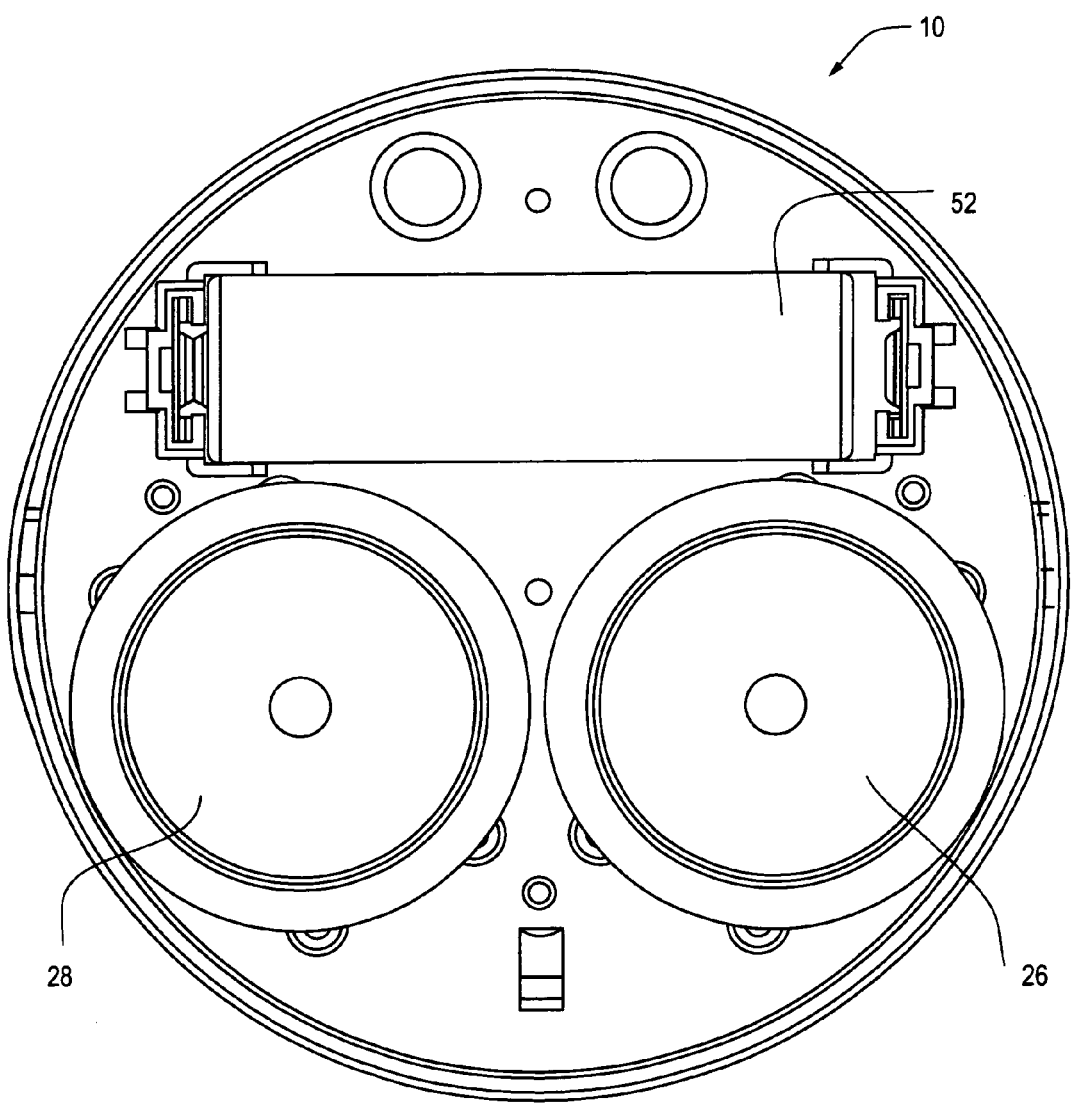
FIG. 11 is a bottom elevational plan view similar to that of FIG. 9 in which the bottom cover is removed.

FIGS. 10 and 11 depict bottom views of the diffusion device 10. FIG. 11 is similar to FIG. 10 except that bottom cover 30 has been removed from FIG. 11. The diffusion device includes a battery 52, which provides direct current to the piezoelectric devices 32 and 34. The battery 52 may be any conventional dry cell battery such as "A", "AA", "AAA", "C", and "D" cells, button cells, watch batteries, and solar cells, but preferably, battery 52 is a "AA" or "AAA" cell battery. Optionally, the diffusion device 10 may be powered by alternating current.

Figure 12:
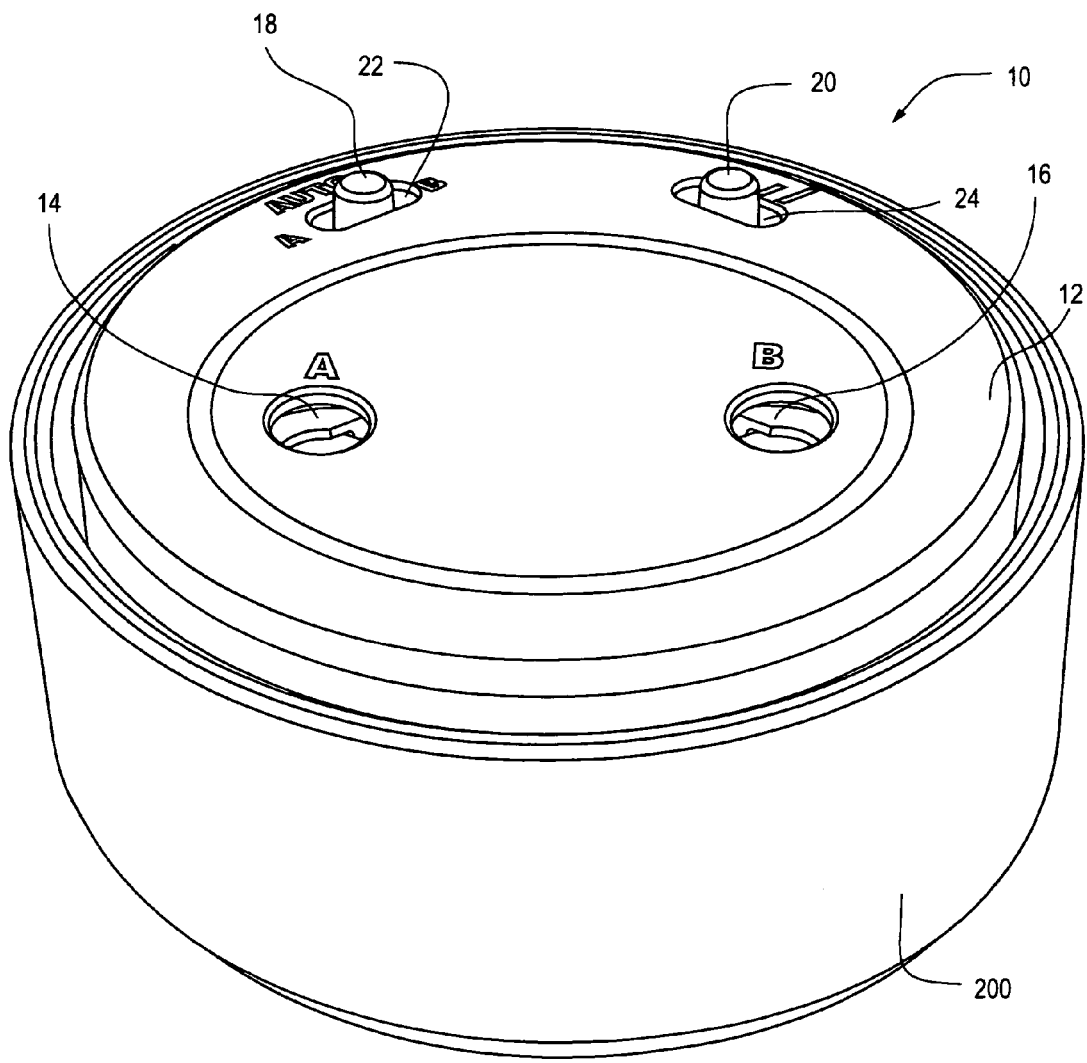
FIG. 12 is a top perspective view of the diffusion device of FIG. 1 disposed within a decorative holder.
Figure 13:
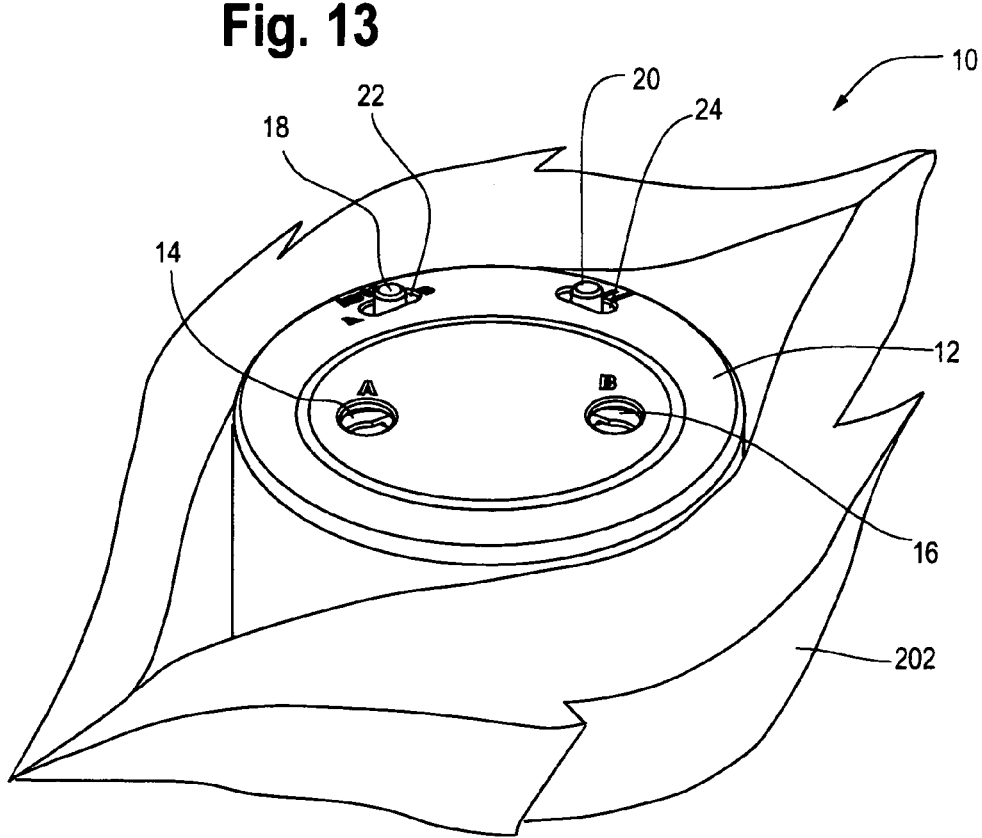
FIG. 13 is a top perspective view similar to that of FIG. 12 in which the diffusion device of FIG. 1 is disposed within an alternative decorative holder.
Figure 14:
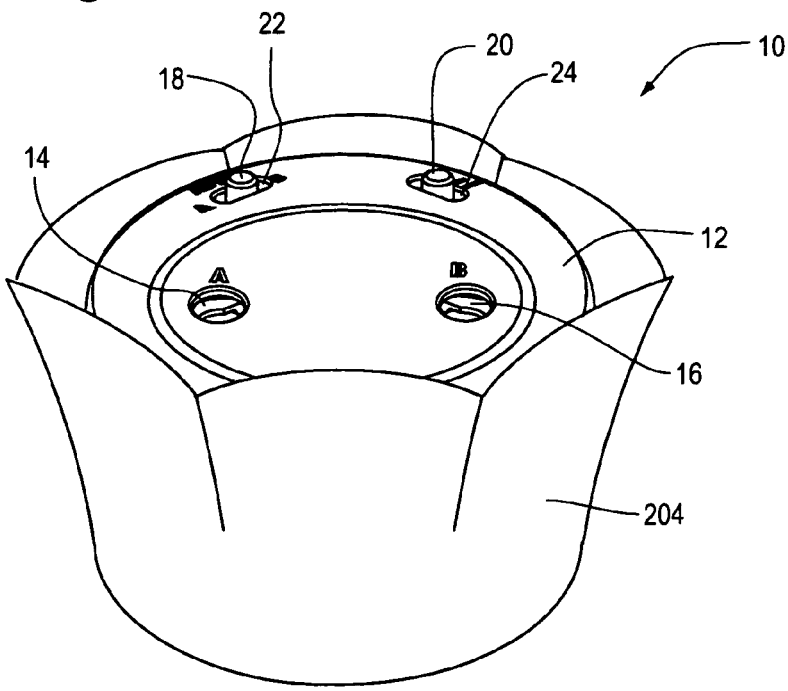
FIG. 14 is a perspective view similar to that of FIGS. 12 and 13 in which the diffusion device of FIG. 1 is disposed within yet an alternative decorative holder.
Figure 15A:
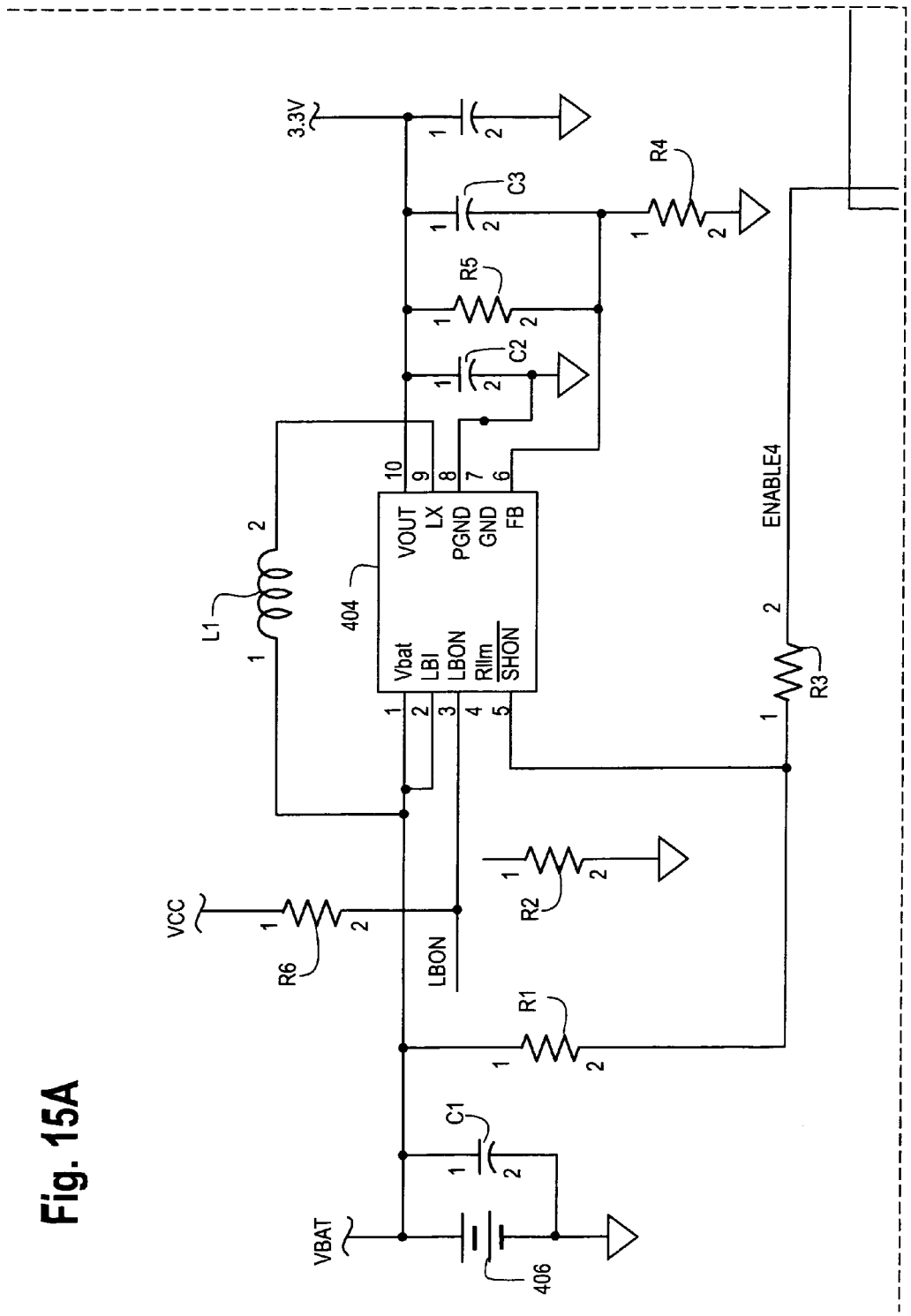
FIGS. 15A-15E, when joined along the dotted lines as shown by FIG. 15, are schematic diagrams illustrating an exemplary circuit for controlling one or more components of the diffusion device of FIG. 1.
Figure 15B:
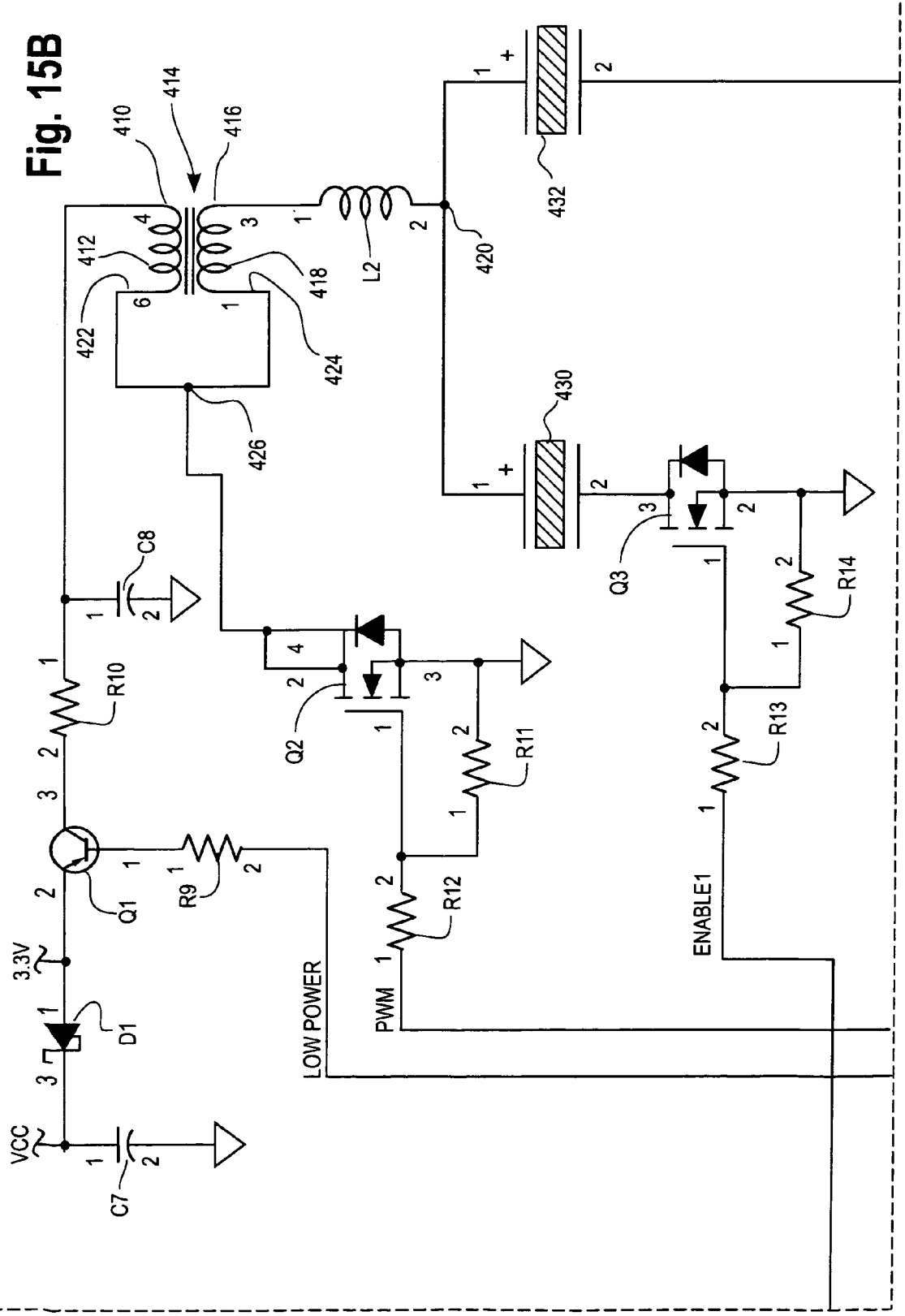
Figure 15C:
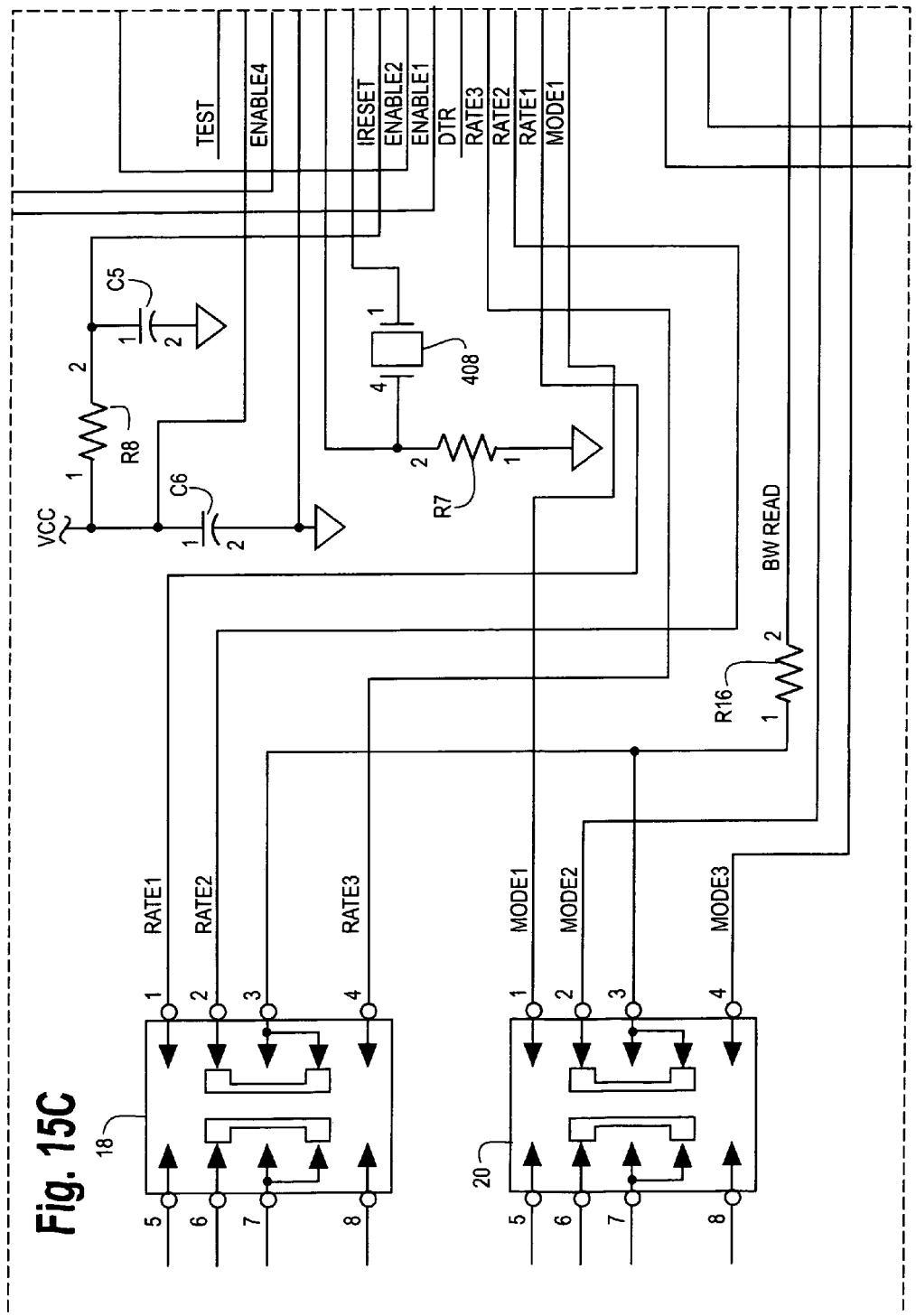
Figure 15D:
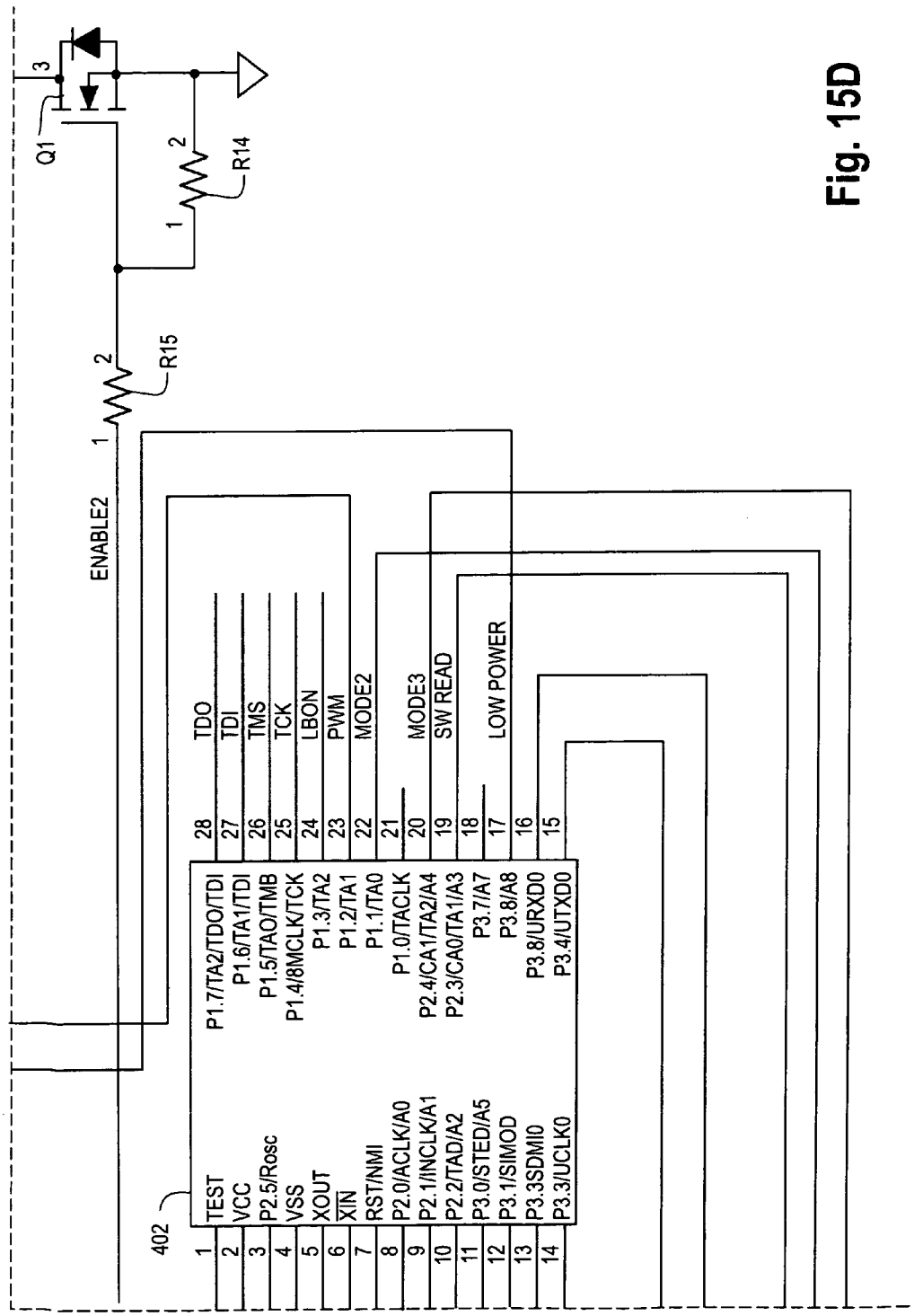
Figure 15E:
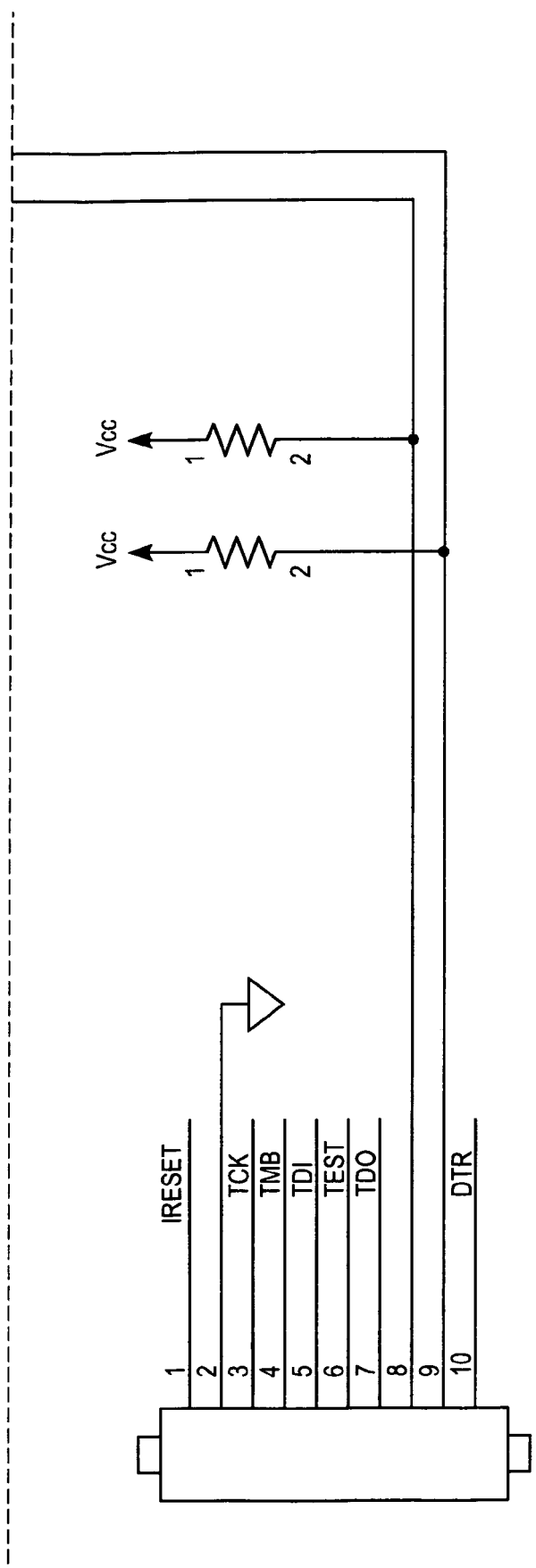

The housing 12 of the diffusion device 10 is preferably generally right circular cylindrically shaped and unadorned, i.e., the housing 12 has a plain, smooth, and regular shape and can be any desired size, but is preferably about 4 inches (10.16 cm) in diameter and is about 2.5 inches (6.35) tall. As shown in FIGS. 12-14, the diffusion device 10 may be disposed within any of numerous decorative holders. As illustrated in FIG. 12, diffusion device 10 may be placed within a cavity of a cylindrical shaped decorative holder 200. Alternatively, diffusion device 10 may be placed within a cavity of a leaf shaped decorative holder 202 as seen in FIG. 13. Yet alternatively, diffusion device 10 may be placed within flower shaped decorative holder 204 as seen in FIG. 14. Alternatively, the decorative holder 200 may be shaped like a pillar candle having the same number of pillars as containers for active materials. Still alternatively, the decorative holder may be shaped like a heart, an animal, a toy, a symbol, or any decorative object.

The decorative holders 200, 202, and 204 are given as illustrations only, as contemplated decorative holders may be of any shape or size and may have any desired design or ornamentation on the exterior and interior surfaces thereof. In addition, such decorative holders may be made from any suitable material including, for example, glass, ceramic and/or plastic such as, for example, nylon, polypropylene, polystyrene, acetal, toughened acetal, polyketone, polybutylene terephthalate, high density polyethylene, polycarbonate, and/or ABS, and combinations thereof.

Optionally, the diffusion device 10 may simple be placed in a decorative holder 200, 202, or 204. In other embodiments, the diffusion device 10 and/or the holder 200, 202, 204 may include means for securing the diffusion device 10 within the holder 200, 202, 204. For example, the diffusion device 10 may be held within the holder 200, 202, 204 by an interference fit therebetween, a frictional fit therebetween, or attachment means may be disposed on one or both of the diffusion device 10 and/or holder 200, 202, 204. Such attachment means may include adhesive tape, hook and loop fasteners, adhesive, or any other attachment means known in the art.

Optionally, one or more of the piezoelectric-type diffusers as disclosed herein may be replaced by any other known diffuser. For example, the piezoelectric devices may be replaced by heated-wick type devices, passive devices, aerosol device, and the like and combinations thereof.

Referring next to FIGS. 15 and 15A-15E, circuitry 400 for operating the device 10 in accordance with a selected mode and selected emission frequency includes a first integrated circuit 402, which may be an application specific integrated circuit (ASIC) or a microprocerssor, and a further integrated circuit 404, preferably a high efficiency boost regulator. The IC 402 may comprise an MSP430FF122 integrated circuit manufactured by Texas Instruments of Dallas, Tex., whereas the integrated circuit 404 may comprise an SP6648 manufactured by Sipex Corporation of Milpitas, Calif. The integrated circuit 404 receives battery power from a AA size battery 406 and develops supply voltages $V_{cc}$ and a 3.3 volt reference level in conjunction with resistors R1-R6, capacitors C1-C4, and inductor L1.

The integrated circuit 402 includes programming to effectuate the control illustrated in FIG. 4 during operation of the device 10 in the "auto" mode of operation.

A pin 3 of the IC 404 is coupled to a pin 24 of the IC 402 for signaling a low-battery condition and a signal ENABLE4 is coupled to a pin 3 and $V_{bat}$ of the IC 402 to ensure normal operation.

The IC 402 includes an internal oscillator that is controlled by a crystal 408 coupled between pins 5 and 6 of the IC 402. A resistor R7 is coupled between one end of the crystal 408 and ground potential. In addition, the IC 402 received the voltage $V_{cc}$ and ground potential at pins 2 and 4 thereof, respectively. A pin of the integrated circuit 402 is coupled to a junction between a resistor R8 and a capacitor C5. A further end of the resistor R8 is coupled to $V_{cc}$ and a capacitor C6 is coupled between $V_{cc}$ and ground. The IC 402 receives a signal SW_READ at a pin 19 thereof via a resistor R16. The signal SW_READ indicates the positions of the switches 18 and 20. More specifically, the signal SW_READ indicates which of pins 13, 12, and 11 (RATE1, RATE2, and RATE3, respectively) is coupled to pin 19 of the IC 402. Further, SW_READ indicates which of pins 14, 20, and 22 (MODE1, MODE2, and MODE3, respectively) are coupled to pin 19 of the IC 402. The signal SW_READ may be read in conjunction with signals RATE1, RATE2, and RATE 3 and signals MODE1, MODE2, and MODE3.

The IC 402 develops a signal LOW_POWER that is delivered through a resistor R9 to the base of a transistor Q1. An emitter of the transistor Q1 receives the 3.3 volt reference. This helps control the charge current delivered to C8 through R10 from the collector of Q1. A Schottky diode D1 is coupled between the emitter of Q1 and $V_{cc}$. A further capacitor C7 is coupled between $V_{cc}$ and ground potential. Capacitor C6 is connected to a first terminal 410 of a primary winding 412 of a transformer 414. A first terminal 416 of a secondary winding 418 of the transformer 414 is coupled through an inductor L2 to a junction 420. Second terminals 422 and 424 of the primary and secondary windings 412, 418, respectively are coupled to a further junction 426. The junction 426 is coupled by a transistor Q2 to ground. A biasing resistor R11 is coupled between gate and source electrodes of the transistor Q2 and the gate electrode receives a control signal PWM through a resistor R12. The signal PWM is developed at a pin 23 of the IC 402.

The junction 420 is coupled to first terminals of piezoelectric elements 430, 432. The piezoelectric element 430 comprises the driving element for the piezoelectric device 32 whereas the piezoelectric element 432 comprises the driving element for the piezoelectric device 34. Second terminals of the piezoelectric elements 430, 432 are coupled by transistors Q3 and Q4, respectively, to ground. A biasing resistor R14 is coupled between the gate and source electrodes of the transistor Q3 and the gate electrode of the transistor Q3 receives a control signal ENABLE1 through a resistor R13. Similarly, a biasing resistor R16 is coupled between the gate and source electrodes of the transistor Q4 and a control signal ENABLE2 is coupled through a resistor R15 to the gate electrode of the transistor Q4. The control signals ENABLE1 and ENABLE2 are developed at pins 9 and 8, respectively, of the IC 402.

Figure 16:
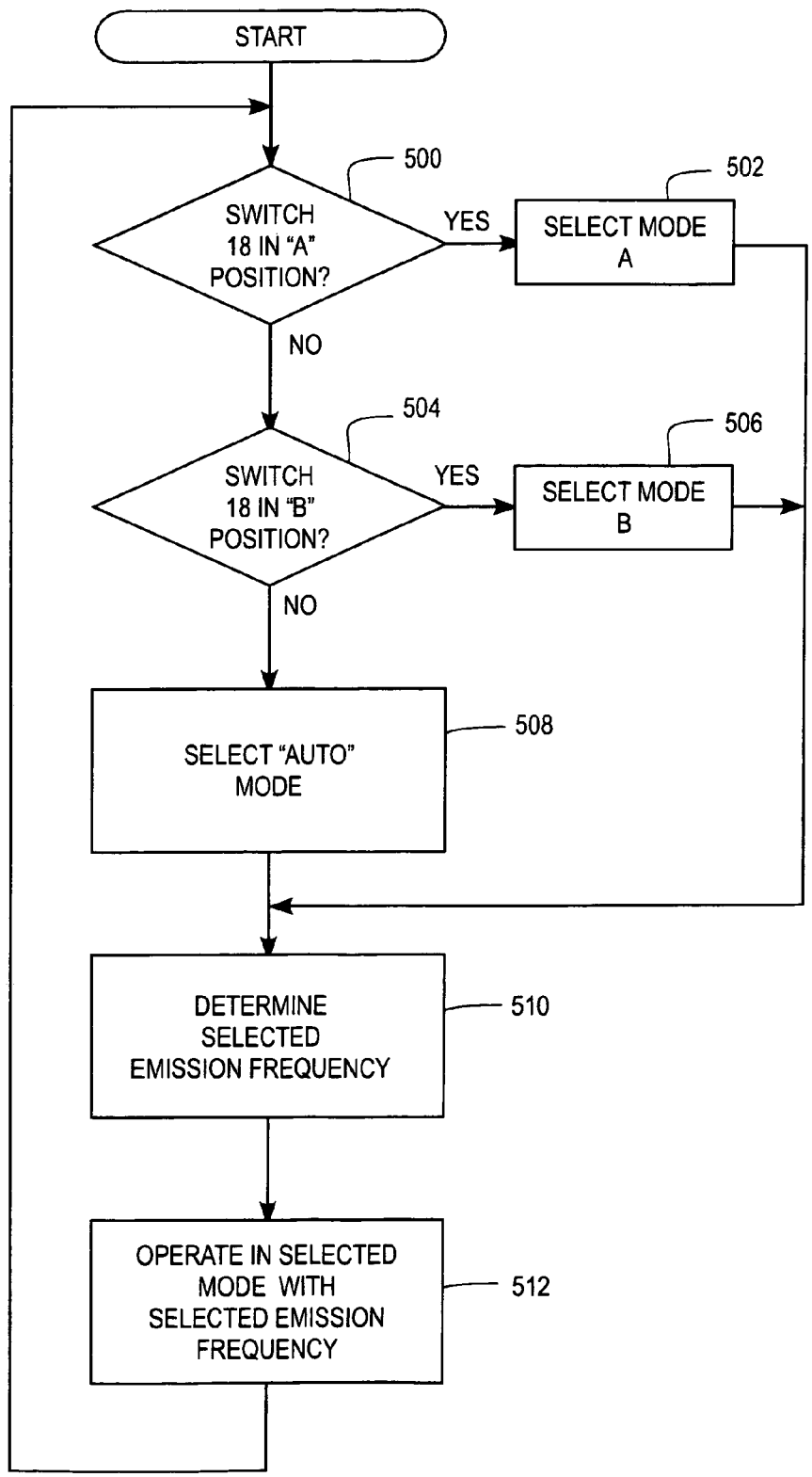
FIG. 16 is a flow diagram illustrating the logic associated with switches for controlling the diffusion device of FIG. 1.

Referring next to the flow chart of FIG. 16, the IC 402 is programmed to cause the device 10 to operate in accordance with a selected mode and emission frequency. As seen in FIG. 16, operation commences at a block 500 which checks to determine whether the switch 18 is in the first position (position "A"). If this is found to be the case, control passes to a block 502 that selects mode A for operation. On the other hand, if the block 500 determines that the switch 18 is not in the first position, then a block 504 checks to determine whether the switch 18 is in the second position (position "B"). If this is the case, then a block 506 selects a mode B of operation. If the block 504 determines that the switch 18 is not in position "B", then it has been determined that the switch 18 is in the "auto" position and a block 508 selects an auto mode of operation. The integrated circuit 402 senses the positions of the switch 18 (and the switch 20, for that matter) by checking SW_READ, which, is noted above, is provided to the pin 19 of the IC 402.

Once the mode has been selected, a block 510 checks the position of the switch 20 in a fashion similar to the blocks 500-508 described above to determine the selected emission frequency. Once the emission frequency has been determined, a block 512 causes the IC 402 to develop the signals LOW_POWER, PWM, ENABLE1, and ENABLE2, in turn to cause the piezoelectric elements, 430, 432 to be energized in accordance with the selected mode of operation and emission frequency. Specifically, a high frequency pulse-width modulated waveform having a frequency between about 130 kHz and about 165 kHz is provided as the control signal PWM, thereby causing the transistor Q2 to rapidly turn on and off, thereby causing high frequency alternating current power to be provided to the junction 420. When the piezoelectric element 430 is to be operated, a high state signal is provided as the signal ENABLE1, thereby turning on the transistor Q3. When the piezoelectric element 432 is to be operated, a high state signal is provided as the signal ENABLE2 thereby turning on the transistor Q4.

When the battery voltage has dropped to a particular level of, for example, 0.8 volts, a high state signal is provided as the LOW_POWER signal, thereby turning off the transistor Q4 and preventing further energization of the piezoelectric elements 430, 432. This feature prevents the battery from being discharged to the point where it would leak and damage the device 10.

In summary, a user may operate the device 10 to emit a selected one of two different active materials for a particular period of time at a selected emission frequency, or may cause the unit to alternate between emissions of different active materials at a selected emission frequency.

INDUSTRIAL APPLICABILITY

The apparatus for and method of dispensing active materials described in the present invention can be used to automatically dispense multiple active materials over an extended period of time, with the added advantage that the frequency of dispersion and the mode of operation may be adjusted. The diffusion device 10 may be placed in any one of a number of different holders to suit the individual preference of the user and/or to disguise the true purpose of the device 10.

Numerous modifications will be apparent to those skilled in the art in view of the foregoing description. Accordingly, this description is to be constructed as illustrative.

We claim:

1. An apparatus for dispensing active materials, comprising:
    a housing; and
    control circuitry disposed within the housing that implements programming for a mode of operation in which during a first sustained period of time a first active material is emitted in the form of discrete bursts each followed by a first dwell period, during a second sustained period of time the first active material is emitted in the form of discrete bursts each followed by a second dwell period and a second active material is emitted in the form of discrete bursts each followed by a third dwell period, wherein during the second sustained period of time the discrete bursts of the first and second active materials are emitted such that when a discrete burst of one of the first and second active materials is emitted, a discrete burst of the other of the first and second active materials is initiated before the discrete burst of the one of the first and second active materials is terminated, and during a third sustained period of time the second active material is emitted in the form of discrete bursts each followed by a fourth dwell period.

2. The apparatus of claim 1, in combination with first and second bottles having first and second active materials therein and first and second wicks in contact with the first and second active materials, respectively, and extending outside of the respective bottles.

3. The apparatus of claim 2, further including first and second piezoelectric devices that are operated by the control circuitry, wherein the first and second piezoelectric elements are in contact with the first and second wicks, respectively, to dispense the first and second fragrances therefrom.

4. The apparatus of claim 1, wherein the control circuitry implements programming for a second mode of operation in which only the first active material is emitted.

5. The apparatus of claim 4, wherein the control circuitry implements programming for a third mode of operation in which only the second active material is emitted.

6. The apparatus of claim 5, wherein a switch is disposed on the housing to allow selection of the first-named, second, or third modes of operation.

7. The apparatus of claim 1, wherein the first and third periods of time have durations that are the same.

8. A method of dispensing active materials, the method comprising the steps of:
    emitting a first active material in the form of discrete bursts each followed by a first dwell period for a first sustained period of time;
    emitting the first active material in the form of discrete bursts each followed by a second dwell period and a second active material in the form of discrete bursts each followed by a third dwell period for a second sustained period of time, wherein during the second sustained period of time the discrete bursts of the first and second active materials are emitted such that when a discrete burst of one of the first and second active materials is emitted, a discrete burst of the other of the first and second active materials is initiated before the discrete burst of the one of the first and second active materials is terminated; and
    emitting the second active material in the form of discrete bursts each followed by a fourth dwell period for a third sustained period of time.

9. The method of claim 8, further including the step of emitting the first active material in the form of discrete bursts each followed by a fifth dwell period and the second active material in the form of discrete bursts each followed by a sixth dwell period for a fourth sustained period of time, wherein during the fourth sustained period of time the discrete bursts of the first and second active materials are emitted such that when a discrete burst of one of the first and second active materials is emitted, a discrete burst of the other of the first and second active materials is initiated before the discrete burst of the one of the first and second active materials is terminated.

10. The method of claim 9, wherein the second sustained period of time follows the first sustained period of time, the third sustained period of time follows the second sustained period of time, and the fourth sustained period of time follows the third sustained period of time.

11. The method of claim 10, wherein the method steps performed during the first, second, third, and fourth sustained periods of time are repeated for a fifth sustained period of time.

12. A method of dispensing active materials, the method comprising the steps of:
    periodically emitting discrete bursts of a first active material for a first sustained period of time;
    periodically emitting discrete bursts of the first active material and a second active material for a second sustained period of time; and
    periodically emitting discrete bursts of the second active material for a third sustained period of time;
    wherein during the second sustained period of time, the discrete bursts of the first and second active materials are alternately emitted such that when a burst of one of the active materials is emitted, a burst of the other of the active materials is initiated before the burst of the one of the active materials is terminated.

13. The method of claim 12, further including the step of periodically emitting discrete bursts of both the first and second active materials for a fourth sustained period of time.

14. The method of claim 13, wherein the discrete bursts of the first and second active materials are alternately emitted during the fourth sustained period of time such that when a burst of one of the active materials is emitted, a burst of the other of the active materials is initiated before the burst of the one of the active materials is terminated.

15. The method of claim 12, wherein a sequence is repeated during the second sustained period of time and the sequence includes bursting the first active material, initiating a burst of the second active material before the burst of the first active material is finished, thereby creating an overlap period, causing delivery of the first active material to enter a dwell period before the second active material is finished bursting, thereafter causing the second active material to enter a dwell period, bursting the second active material, initiating a burst of the first active material before the burst of the second active material is concluded, causing the second active material to enter a dwell period before the burst of the first active material is terminated, and thereafter causing the first active material to enter a dwell period.

16. The method of claim 15, wherein a sequence is repeated during the fourth sustained period of time and the sequence includes bursting the second active material, initiating a burst of the first active material before the burst of the second active material is finished, thereby creating an overlap period, causing the second active material to enter a dwell period before the first active material is finished bursting, causing delivery of the first active material to enter a dwell period, bursting the first active material, initiating a burst of the second active material before the burst of the first active material is concluded, causing the first active material to enter a dwell period before the burst of the second active material is terminated, and thereafter causing the second active material to enter a dwell period.

17. The method of claim 12, wherein the second sustained period of time follows the first sustained period of time and the third sustained period of time follows the first sustained period of time.

* * * * *

UNITED STATES PATENT AND TRADEMARK OFFICE
CERTIFICATE OF CORRECTION

PATENT NO. : 7,622,073 B2  Page 1 of 1
APPLICATION NO. : 11/427714
DATED : November 24, 2009
INVENTOR(S) : Schramm et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 420 days.

Signed and Sealed this

Twenty-sixth Day of October, 2010

David J. Kappos
*Director of the United States Patent and Trademark Office*